US012653637B2

(12) United States Patent
Lin et al.

(10) Patent No.: US 12,653,637 B2
(45) Date of Patent: Jun. 16, 2026

(54) INSTRUMENT RETRACTION FACILITATION

(71) Applicant: Auris Health, Inc., Santa Clara, CA (US)

(72) Inventors: Jiayi Lin, San Mateo, CA (US); Chauncey F. Graetzel, Palo Alto, CA (US); John Raymond Young, San Mateo, CA (US)

(73) Assignee: Auris Health, Inc., Santa Clara, CA (US)

( * ) Notice: Subject to any disclaimer, the term of this patent is extended or adjusted under 35 U.S.C. 154(b) by 20 days.

(21) Appl. No.: 18/810,076

(22) Filed: Aug. 20, 2024

(65) Prior Publication Data

US 2024/0415599 A1     Dec. 19, 2024

Related U.S. Application Data

(62) Division of application No. 17/335,341, filed on Jun. 1, 2021, now Pat. No. 12,097,079.

(Continued)

(51) Int. Cl.
| | |
|---|---|
| *A61B 90/00* | (2016.01) |
| *A61B 17/00* | (2006.01) |

(Continued)

(52) U.S. Cl.
CPC ........ *A61B 90/06* (2016.02); *A61B 17/00234* (2013.01); *A61B 17/221* (2013.01);

(Continued)

(58) Field of Classification Search
CPC ............ A61B 17/00234; A61B 17/221; A61B 2017/00119; A61B 2017/0034;

(Continued)

(56) References Cited

U.S. PATENT DOCUMENTS

| | | |
|---|---|---|
| 5,176,688 A | 1/1993 | Narayan et al. |
| 5,944,728 A | 8/1999 | Bates et al. |

(Continued)

FOREIGN PATENT DOCUMENTS

| | | |
|---|---|---|
| CN | 108124423 A | 6/2018 |
| WO | 199848710 A1 | 11/1998 |

(Continued)

OTHER PUBLICATIONS

Office Action from China Patent Application No. 202180039532.4, dated Aug. 7, 2025, 28 pages.

(Continued)

*Primary Examiner* — Mohamed G Gabr
(74) *Attorney, Agent, or Firm* — Paradice & Li LLP

(57) ABSTRACT

A robotic system includes one or more robotic manipulators, one or more actuators associated with at least one of the one or more robotic manipulators, one or more sensors associated with the one or more robotic manipulators and configured to generate signals indicating a force experienced by the one or more actuators, and control circuitry communicatively coupled to the one or more robotic manipulators and the one or more sensors. The control circuitry is configured to cause the basket device to advance and retract in a dithering motion, while the basket device is moving in the dithering motion, receive the signals from the one or more sensors indicating the force experienced by the one or more actuators, determine that the force is greater than a predetermined threshold, and execute a responsive action in response to the determination that the force is greater than the predetermined threshold.

20 Claims, 19 Drawing Sheets

Related U.S. Application Data

(60) Provisional application No. 63/033,089, filed on Jun. 1, 2020.

(51) Int. Cl.

| | |
|---|---|
| *A61B 17/221* | (2006.01) |
| *A61B 34/30* | (2016.01) |
| *A61B 34/37* | (2016.01) |

(52) U.S. Cl.
CPC ..... *A61B 34/30* (2016.02); *A61B 2017/00119* (2013.01); *A61B 2017/0034* (2013.01); *A61B 2034/301* (2016.02); *A61B 34/37* (2016.02); *A61B 2090/064* (2016.02)

(58) Field of Classification Search
CPC ...... A61B 2017/2212; A61B 2034/301; A61B 2090/064; A61B 34/30; A61B 34/35; A61B 34/37; A61B 90/06
See application file for complete search history.

(56) References Cited

U.S. PATENT DOCUMENTS

| | | | |
|---|---|---|---|
| 7,645,283 | B2 | 1/2010 | Reynolds et al. |
| 9,955,986 | B2 | 5/2018 | Shah |
| 11,504,187 | B2 | 11/2022 | Walker et al. |
| 12,097,079 | B2 | 9/2024 | Lin et al. |
| 2002/0042617 | A1 | 4/2002 | Ouchi |
| 2002/0091394 | A1 | 7/2002 | Reynolds et al. |
| 2005/0261705 | A1 | 11/2005 | Gist |
| 2007/0197939 | A1 | 8/2007 | Wallace et al. |
| 2007/0233044 | A1 | 10/2007 | Wallace et al. |
| 2014/0288525 | A1 | 9/2014 | Fudaba et al. |
| 2016/0374702 | A1* | 12/2016 | St. George ........... A61B 17/221 606/127 |
| 2017/0119411 | A1 | 5/2017 | Shah |
| 2017/0119481 | A1* | 5/2017 | Romo ................ A61B 1/00096 |
| 2017/0172668 | A1 | 6/2017 | Aljuri et al. |
| 2017/0303945 | A1 | 10/2017 | George et al. |
| 2018/0177561 | A1 | 6/2018 | Mintz et al. |
| 2018/0221035 | A1 | 8/2018 | Chu |
| 2019/0175009 | A1 | 6/2019 | Mintz et al. |
| 2019/0175799 | A1* | 6/2019 | Hsu ..................... A61M 3/0202 |
| 2019/0350603 | A1 | 11/2019 | Bonneau et al. |
| 2019/0380791 | A1 | 12/2019 | Fuerst et al. |

FOREIGN PATENT DOCUMENTS

| | | | |
|---|---|---|---|
| WO | 2007098494 | A1 | 8/2007 |
| WO | 2014127353 | A1 | 8/2014 |
| WO | 2015134846 | A1 | 9/2015 |
| WO | 2016209318 | A1 | 12/2016 |
| WO | 2017075574 | A1 | 5/2017 |
| WO | 2018125917 | A1 | 7/2018 |

OTHER PUBLICATIONS

Office Action from Japan Patent Application No. 2022-573691, dated Jul. 22, 2025, 9 pages.

Office Action from Korean Patent Application No. 10-2022-7046080, dated Dec. 2, 2025, 8 pages.

Office Action from Japan Patent Application No. 2022-573691, dated Jan. 7, 2025, 9 pages.

EP Search Report for Appl. No. 21818272.3, dated May 31, 2024, 8 pages.

Non-Final Rejection for U.S. Appl. No. 17/335,341, dated Feb. 1, 2024, 6 pages.

Corrected Notice of Allowability for U.S. Appl. No. 17/335,341, dated Jun. 20, 2024, 2 pages.

Notice of Allowance for U.S. Appl. No. 17/335,341, dated May 22, 2024, 8 pages.

Search report for appl No. PCTIB2021054800, dated Sep. 7, 2021, 4 pages.

Written Opinion for appl No. PCTIB2021054800, dated Sep. 7, 2021, 4 pages.

Second Office Action from China Patent Application No. 202180039532.4, dated Dec. 18, 2025, 19 pages.

Notification to Grant Patent Right for Invention from China Patent Application No. 202180039532.4, dated Feb. 27, 2026, 6 pages.

* cited by examiner

80

70

40
71
78
90

63

40

42  48  30

90

45  44

49  35

35a  35b  35c  35d  35e

335

309
308

60

65

90

311  90  312

11

40

19  37

36

32  31

7

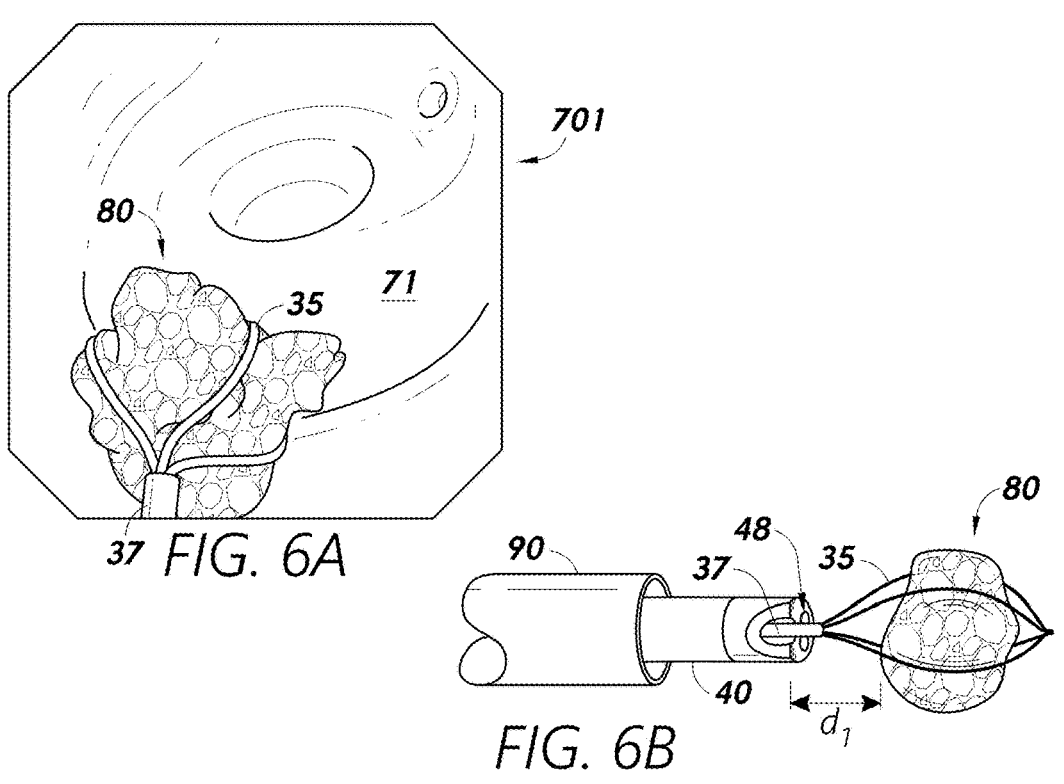
FIG. 6A
FIG. 6B
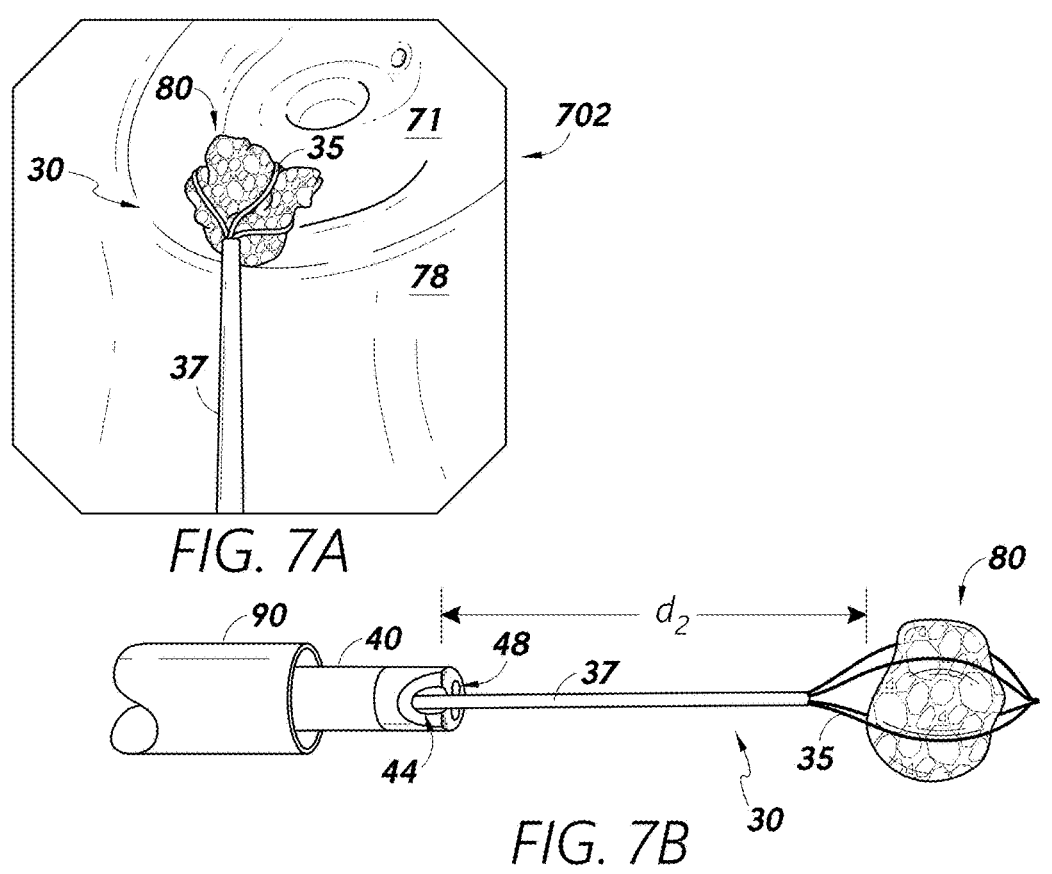
FIG. 7A
FIG. 7B

*901*
CAPTURE STONE

*902*
RETRACT SCOPE/BASKET INTO STUCK INSTRUMENT HAZARD ZONE

*904*
ACTIVATE BASKET DITHER

*906*
RETRACT THROUGH UPJ / URETER OSTIUM

STUCK INSTRUMENT DETECTED

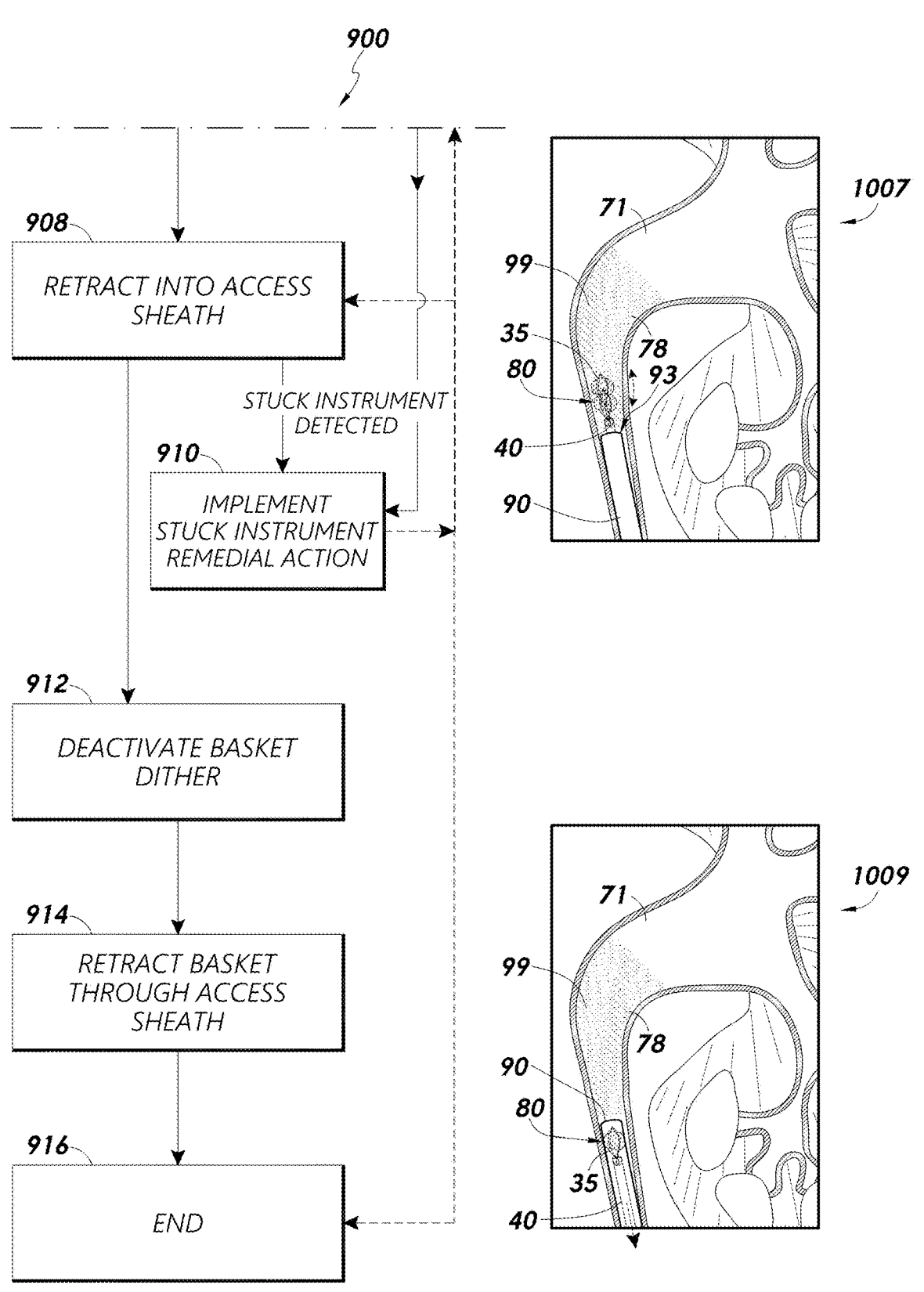
*FIG. 9-2*                          *FIG. 10-2*

*HANDLING OF FALSE POSITIVE ON INSERTION AXIS*

DITHER DIAGRAM

DITHER ZONE ADJUSTMENT - HARD STOP CONTACT ON INSERT

DITHER ZONE ADJUSTMENT – HARD STOP CONTACT ON RETRACT

*HANDLING OF FALSE POSITIVE ON OPEN AXIS*

2000

2002 CAPTURE STONE

2004 RETRACT SCOPE WITH BASKET

2006 ELEVATED FORCE DETECTED ON INSERTION AXIS?

YES → 2010 DRIVE FORWARD SOFT STOP BUFFER DISTANCE

STUCK INSTRUMENT CONDITION → 2016 IMPLEMENT STUCK INSTRUMENT REMEDIAL ACTION / 2011 USER ACKNOWLEDGEMENT

NO → 2012 COLLECT STONE

2019 ADDITIONAL STONE(S)?

NO → END

YES → 2018 INSERT SCOPE / BASKET

INSTRUMENT RETRACTION FACILITATION

RELATED APPLICATION(S)

This application is a divisional of U.S. application Ser. No. 17/335,341, filed Jun. 1, 2021, now U.S. Pat. No. 12,097,079, and entitled STUCK INSTRUMENT MANAGEMENT, which claims priority to U.S. Provisional Application No. 63/033,089, filed Jun. 1, 2020, and entitled STUCK INSTRUMENT MANAGEMENT, the disclosures of which are hereby incorporated by reference in their entireties.

BACKGROUND

Field

The present disclosure relates to the field of medical instruments and procedures.

Description of Related Art

Various medical procedures involve the use of one or more medical instruments in an anatomical cavity. The retraction and/or removal of such instrument(s) from the anatomical cavity can present certain complications resulting in damage to biological tissue, instrument component(s), and/or other adverse outcomes.

SUMMARY

Described herein are systems, devices, and methods to facilitate the management and/or determination of stuck-instrument conditions in connection with the execution of certain medical procedure steps, such as instrument retraction.

In some implementations, the present disclosure relates to a method of detecting a stuck basket condition. The method comprises retracting an endoscope within an anatomical cavity of a patient, the endoscope having a basket device disposed at least partially within a working channel thereof, determining that a force reading associated with at least one of the basket device and the endoscope exceeds a predetermined threshold, and determining that the basket device is in a stuck condition based at least in part on the determination that the force reading exceeds the predetermined threshold.

The method can further comprise axially dithering the basket device, wherein determining that the force reading associated with the at least one of the basket device and the endoscope exceeds the predetermined threshold is performed while dithering the basket device. The method can further comprise accessing the anatomical cavity with the endoscope via urinary tract anatomy of the patient, advancing the basket device from the working channel of the endoscope, capturing an object disposed within the anatomical cavity with the basket device, determining that the at least one of the basket device and the endoscope has entered a hazard zone, and, in response to said determining that the at least one of the basket device and the endoscope has entered the hazard zone, initiating the axial dithering of the basket device. For example, determining that the at least one of the basket device and the endoscope has entered the hazard zone is based at least in part on robotic actuator data generated by one or more robotic actuators configured to actuate one or more of the endoscope and the basket device. In some implementations, determining that the at least one of the basket device and the endoscope has entered the hazard zone is based at least in part on positional sensor data associated with one or more of the endoscope and the basket device. In some embodiments, the hazard zone includes a ureteropelvic junction of a kidney of the patient. Dithering of the basket device may be relative to a distal end of the endoscope. Dithering of the basket can involve dithering the endoscope.

The method may further comprise reducing a retraction speed of the endoscope based at least in part on the determined stuck condition of the basket device. In some embodiments, the force reading indicates an axial force experienced at a proximal portion of a sheath of the basket device. In some embodiments, the force reading indicates an axial force on one or more tines of the basket device. In some embodiments, the force reading indicates an axial force experienced at a proximal portion of the endoscope. The method may further comprise causing a warning to be presented in response to the determined stuck condition.

In some implementations, the present disclosure relates to a robotic system comprising one or more robotic arms, one or more instrument manipulators coupled to respective ones of the one or more robotic arms, one or more actuators associated with at least one of the one or more instrument manipulators and configured to cause axial movement of at least one of an endoscope, a sheath of a basket device disposed at least partially within the endoscope, and tines of the basket device, one or more sensors associated with the one or more instrument manipulators and configured to generate signals indicating a force experienced by the one or more actuators, and control circuitry communicatively coupled to the one or more instrument manipulators and the one or more sensors and configured to cause the basket device to advance and retract in a dithering motion, receive the signals from the one or more sensors indicating the force experienced by the one or more actuators while the basket device is moving in the dithering motion, determine that the force is greater than a predetermined threshold, and execute a responsive action in response to the determination that the force is greater than the predetermined threshold.

The responsive action may involve providing a warning to a user indicating that the basket device is in a stuck state. In some embodiments, the responsive action involves reducing a retraction speed of the endoscope. In some embodiments, the responsive action involves halting retraction of the endoscope. The one or more actuators may comprise one or more basket sheath actuators. In some embodiments, the one or more actuators comprise one or more basket tine actuators. In some embodiments, the one or more actuators comprise one or more endoscope actuators. The one or more sensors can be configured to determine at least one of insertion and retraction force relating to the endoscope.

In some implementations, the present disclosure relates to a method of detecting a stuck condition for a medical instrument. The method comprises determining that a force on a component of the medical instrument is greater than a predetermined force threshold while a medical instrument is retracted in a dithering motion, initiating a timer in response to the determination that the force is greater than the predetermined threshold, determining that the timer has passed a predetermined time threshold, and initiating a responsive action in response to the determination that the timer has passed the predetermined time threshold.

The responsive action may involve generating a warning indicating that the medical instrument is in a stuck state. The responsive action may involve halting retraction of the medical instrument. The method can further comprise initiating dithering of one or more components of the medical instrument in response to a determination that a portion of the medical instrument is positioned within a sticking hazard zone. For example, the method may further comprise determining the sticking hazard zone based at least in part on a position of a distal end of a sheath in which the medical instrument is a least partially disposed.

In some implementations, the present disclosure relates to a computing device comprising a robotic system interface and control circuitry communicatively coupled to the robotic system interface and comprising one or more processors and one or more data storage devices. The control circuitry can be configured to cause a basket device to be dithered relative to a working channel of an endoscope in which the basket device is at least partially disposed and, while the basket device is dithering, determine that a force experienced by one or more components of the basket device indicates a stuck state of the basket device.

The determination that the force indicates the stuck state may be based on one or more of data indicating a driving behavior of a user driving the endoscope and a size of an object captured by the basket device. In some embodiments, the control circuitry is further configured to disable dithering of the basket in response to a determination that the basket device and the endoscope have been retracted within an access sheath. In some embodiments, the control circuitry is further configured to halt motion of the endoscope in response to the stuck state.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIG. 6A shows a field-of-view of an endoscope camera with a basketing device viewable therein in accordance with one or more embodiments.

FIG. 6B shows a side view of a medical instrument assembly corresponding to the configuration of the basketing device relative to the endoscope camera of FIG. 6A in accordance with one or more embodiments.

FIG. 7A shows a field-of-view of an endoscope camera with a basketing device in a stuck condition viewable therein in accordance with one or more embodiments.

FIG. 7B shows a side view of a medical instrument assembly corresponding to the configuration of the basketing device relative to the endoscope camera of FIG. 7A in accordance with one or more embodiments.

FIG. 8 illustrates a stuck-instrument image recognition architecture in accordance with one or more embodiments.

FIGS. 9-1 and 9-2 show a flow diagram illustrating a process for managing stuck-instrument conditions in accordance with one or more embodiments.

FIGS. 10-1 and 10-2 shows certain images corresponding to various blocks, states, and/or operations associated with the process of FIGS. 9-1 and 9-2 in accordance with one or more embodiments.

DETAILED DESCRIPTION

Figure 1:
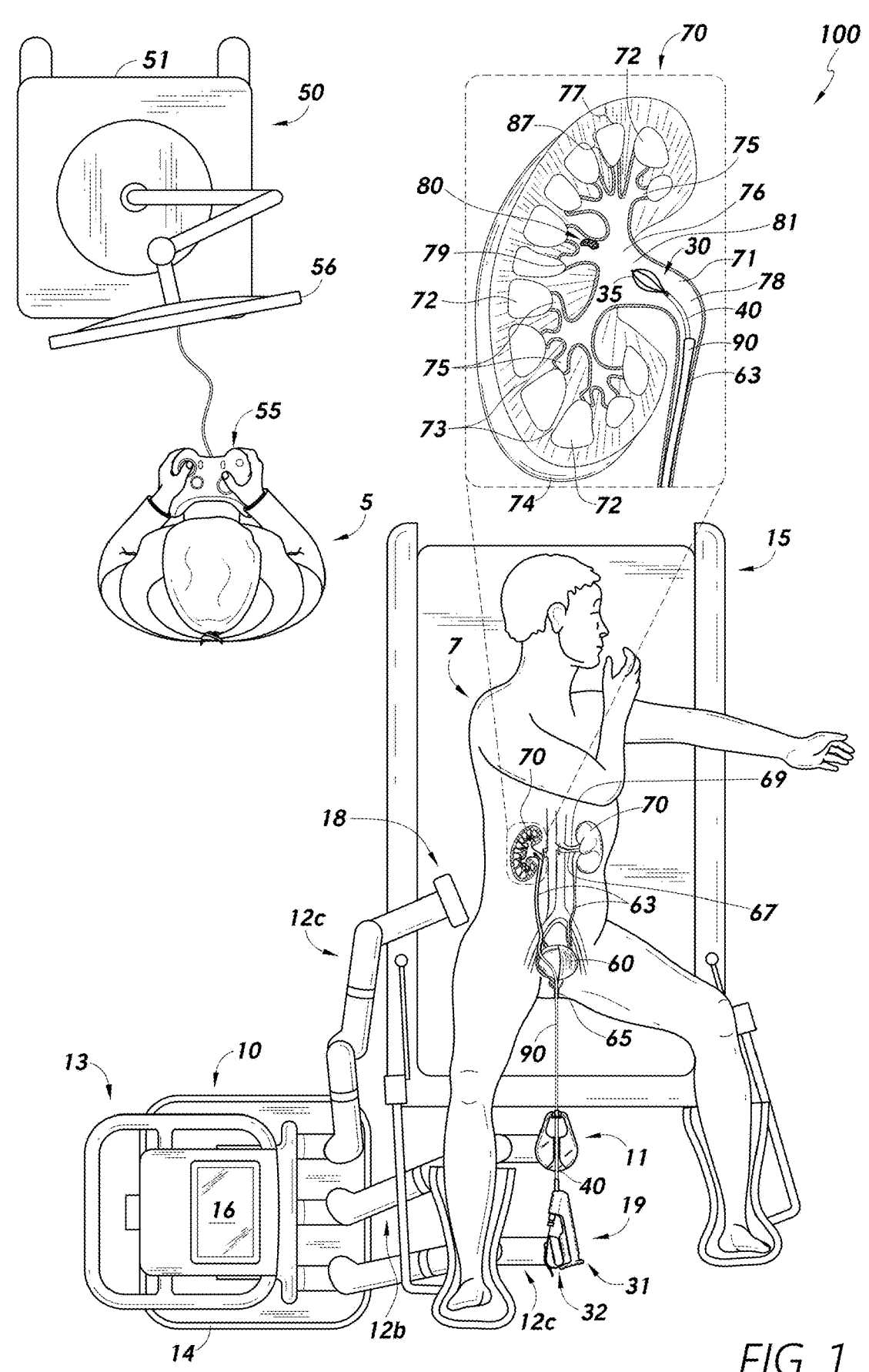
FIG. 1 illustrates an embodiment of a medical system including one or more basketing components in accordance with one or more embodiments.

The headings provided herein are for convenience only and do not necessarily affect the scope or meaning of the claimed invention. Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Overview

The present disclosure relates to systems, devices, and methods for managing medical instrument retraction and/or advancement in patient anatomy, such as during execution of a medical procedure. Although certain aspects of the present disclosure are described in detail herein in the context of renal, urological, and/or nephrological procedures, such as kidney stone removal/treatment procedures, it should be understood that such context is provided for convenience and clarity, and stuck-instrument determination and/or instrument retraction/advancement concepts disclosed herein are applicable to any suitable medical procedures. However, as mentioned, description of the renal/urinary anatomy and associated medical issues and procedures is presented below to aid in the description of the inventive concepts disclosed herein.

Kidney stone disease, also known as urolithiasis, is a medical condition that involves the formation in the urinary tract of a solid piece of material, referred to as "kidney stones," "urinary stones," "renal calculi," "renal lithiasis," or "nephrolithiasis." Urinary stones may be formed and/or found in the kidneys, the ureters, and the bladder (referred to as "bladder stones"). Such urinary stones can form as a result of mineral concentration in urinary fluid and can cause significant abdominal pain once such stones reach a size sufficient to impede urine flow through the ureter or urethra. Urinary stones may be formed from calcium, magnesium, ammonia, ur acid, cysteine, and/or other compounds or combinations thereof.

Generally, there are several methods for treating patients with kidney stones, including observation, medical treatments (such as expulsion therapy), non-invasive treatments (such as extracorporeal shock wave lithotripsy (ESWL)), and surgical treatments (such as ureteroscopy and percutaneous nephrolithotomy ("PCNL")). In surgical approaches (e.g., ureteroscopy and PCNL), the physician gains access to the object to be removed (e.g., a kidney stone), the object is broken into smaller pieces or fragments, and the relatively small stone fragments/particulates are mechanically extracted from the kidney.

To remove urinary stones from the bladder and ureter, surgeons may insert a ureteroscope into the urinary tract through the urethra. Typically, a ureteroscope includes a scope/camera at its distal end configured to enable visualization of the urinary tract. The ureteroscope can also include a lithotripsy device to capture or break apart urinary stones. During a ureteroscopy procedure, one physician/technician may control the position of the ureteroscope, while another physician/technician may control the lithotripsy device(s).

In order to remove relatively large stones from the kidneys, physicians may use a percutaneous nephrolithotomy ("PCNL") technique that involves inserting a nephroscope through the skin (i.e., percutaneously) and intervening tissue to provide access to the treatment site for breaking-up and/or removing the stone(s). A percutaneous access instrument (e.g., nephroscope, sheath, and/or catheter) used to provide an access channel to the target anatomical site (and/or a direct-entry endoscope) may include one or more fluid channels for providing irrigation fluid flow to the target site and/or aspirating fluid from the target site (e.g., through passive outflow and/or active suction).

Robotic devices and/or systems can be employed in connection with various medical procedures, such as kidney stone removal procedures, wherein robotic tools can enable a physician/urologist to perform endoscopic (e.g., ureteroscopy) target access, percutaneous access/treatment, or other aspects of a medical procedure. Advantageously, aspects of the present disclosure relate to systems, devices, and methods for utilizing robotic devices and systems to detect and manage stuck-instrument conditions. The terms "stuck instrument," "stuck basket," "stuck stone," "caught instrument," "caught basket," and "caught stone" are used herein according to their broad and ordinary meanings and may refer to any condition or occurrence in which at least a portion of a medical instrument or pathology (e.g., kidney stone or other object for removal) becomes at least partially impeded, obstructed, blocked, caught, stuck, inhibited or otherwise prevented from continuous movement during advancement or retraction thereof in some manner.

Advancement and retraction of a ureteroscope and/or associated basketing device during a ureteroscopy can result in damage to certain anatomical features and/or components of one or more medical instruments utilized in a procedure. For example, in instances in which a kidney stone or other object is extracted or attempted to be extracted, wherein the stone/object is larger with respect one or more dimensions thereof than the size/dimension of the ureter and/or ureteral access sheath used to access the target anatomy, tearing or other damage to the ureteral/renal tissue may result at or near locations in which the stone/object, and/or basket component in which the stone/object is captured, contact the tissue due at least in part to, for example, the size of the stone/object.

In several of the examples described herein, object removal procedures relate to removal of kidney stones from a kidney. This disclosure, however, is not limited only to kidney stone removal and associated instrumentation. For example, the following description is also applicable to other surgical or medical operations or medical procedures concerned with the removal of objects from a patient, including any object that can be removed from a treatment site or patient cavity (e.g., the esophagus, ureter, intestine, eye, etc.) via percutaneous and/or endoscopic access, such as, for example, gallbladder stone removal, lung (pulmonary/transthoracic) tumor biopsy, or cataract removal. That is, stuck instrument management concepts disclosed herein are applicable to instruments that may become stuck during any of such procedures.

Medical System

FIG. 1 illustrates an example medical system 100 for performing various medical procedures in accordance with aspects of the present disclosure. The medical system 100 may be used for, for example, endoscopic (e.g., ureteroscopic) procedures. As referenced and described above, certain ureteroscopic procedures involve the treatment/removal of kidney stones. In some implementations, kidney stone treatment can benefit from the assistance of certain robotic technologies/devices, such as may be similar to those shown in FIG. 1 and described in detail below. Robotic medical solutions can provide relatively higher precision, superior control, and/or superior hand-eye coordination with respect to certain instruments compared to strictly-manual procedures. For example, robotic-assisted ureteroscopic access to the kidney in accordance with some procedures can advantageously enable a urologist to perform both endoscope control and basketing control.

Although the system 100 of FIG. 1 is presented in the context of a ureteroscopic procedure, it should be understood that the principles disclosed herein may be implemented in any type of endoscopic and/or percutaneous procedure. Furthermore, several of the examples described herein relate to object removal procedures involving the removal of kidney stones from a kidney. The present disclosure, however, is not limited only to kidney stone removal. For example, the following description is also applicable to other surgical or medical operations or medical procedures concerned with the removal of objects from a patient, including any object that can be removed from a treatment site or patient cavity (e.g., the esophagus, ureter, intestine, eye, etc.) via percutaneous and/or endoscopic access, such as, for example, gallbladder stone removal, lung (pulmonary/transthoracic) tumor biopsy, or cataract removal.

The medical system 100 includes a robotic system 10 (e.g., mobile robotic cart) configured to engage with and/or control a medical instrument 40 (e.g., ureteroscope) to perform a direct-entry procedure on a patient 7. The term "direct-entry" is used herein according to its broad and ordinary meaning and may refer to any entry of instrumentation through a natural or artificial opening in a patient's body. For example, with reference to FIG. 1, the direct entry of the scope 40 into the urinary tract of the patient 7 may be made via the urethra 65.

It should be understood that the direct-entry instrument 40 may be any type of medical instruments, including an endoscope (such as a ureteroscope), catheter (such as a steerable or non-steerable catheter), nephroscopes, laparoscope, or other type of medical instrument. Embodiments of the present disclosure relating to basketing solutions implemented in connection with ureteroscopic procedures for removal of kidney stones through a ureteral access sheath (e.g., the ureteral access sheath 90) are also applicable to solutions for removal of objects through percutaneous access, such as through a percutaneous access sheath. For example, instrument(s) may access the kidney percutaneously through, for example, a percutaneous access sheath to capture and remove kidney stones; instruments used to capture such stones may become stuck on the internal renal anatomy and/or the percutaneous access sheath (e.g., at an opening of the percutaneous access sheath). The term "percutaneous access" is used herein according to its broad and ordinary meaning and may refer to entry, such as by puncture and/or minor incision, of instrumentation through the skin of a patient and any other body layers necessary to reach a target anatomical location associated with a procedure (e.g., the calyx network of the kidney 70).

The medical system 100 includes a control system 50 configured to interface with the robotic system 10, provide information regarding the procedure, and/or perform a variety of other operations. For example, the control system 50 can include one or more display(s) 56 configured to present certain information to assist the physician 5 and/or other technician(s) or individual(s). The medical system 100 can include a table 15 configured to hold the patient 7. The system 100 may further include an electromagnetic (EM) field generator 18, which may be held by one or more of the robotic arms 12 of the robotic system 10 or may be a stand-alone device. Although the various robotic arms are shown in various positions and coupled to various instrumentation, it should be understood that such configurations are shown for convenience and illustration purposes, and such robotic arms may have different configurations over time and/or at different points during a medical procedure. Furthermore, the robotic arms 12 may be coupled to different instruments than shown in FIG. 1, and in some cases or periods of time, one or more of the arms may not be utilized or coupled to a medical instrument (e.g., instrument manipulator/coupling).

In an example use case, if the patient 7 has a kidney stone 80 located in the kidney 70, the physician may execute a procedure to remove the stone 80 through the urinary tract (63, 60, 65). In some embodiments, the physician 5 can interact with the control system 50 and/or the robotic system 10 to cause/control the robotic system 10 to advance and navigate the medical instrument 40 (e.g., a scope) from the urethra 65, through the bladder 60, up the ureter 63, and into the renal pelvis 71 and/or calyx network of the kidney 70 where the stone 80 is located. The physician 5 can further interact with the control system 50 and/or the robotic system 10 to cause/control the advancement of a basketing device 30 through a working channel of the instrument 40, wherein the basketing device 30 is configured to facilitate capture and removal of a kidney stone. The control system 50 can provide information via the display(s) 56 that is associated with the medical instrument 40, such as real-time endoscopic images captured therewith, and/or other instruments of the system 100, to assist the physician 5 in navigating/controlling such instrumentation.

The renal anatomy is described herein for reference with respect to certain medical procedures relating to aspects of the present inventive concepts. The kidneys 70, shown roughly in typical anatomical position in FIG. 1, generally comprise two bean-shaped organs located on the left and right sides, respectively, in the retroperitoneal space. In adult humans, the kidneys are generally about 11 cm in height/length. The kidneys receive blood from the paired renal arteries 69; blood exits the kidney via the paired renal veins 67. Each kidney 70 is fluidly coupled with a respective ureter 63, which generally comprises a tube that carries excreted urine from the kidney 70 to the bladder 60.

The kidneys 70 are typically located relatively high in the abdominal cavity and lie in a retroperitoneal position at a slightly oblique angle. The asymmetry within the abdominal cavity, generally caused by the position of the liver, results in the right kidney (shown in detail in FIG. 1) typically being slightly lower and smaller than the left, and being placed slightly more to the middle than the left kidney. On top of each kidney is an adrenal gland (not shown). The upper parts of the kidneys 70 are partially protected by the 11th and 12th ribs (not shown). Each kidney, with its adrenal gland, is generally surrounded by two layers of fat: the perirenal fat present between renal fascia and renal capsule and pararenal fat superior to the renal fascia.

The kidneys 70 participate in the control of the volumes of various body fluid compartments, fluid osmolality, acid-base balance, various electrolyte concentrations, and removal of toxins. The kidneys 70 provide filtration functionality by secreting certain substances and reabsorbing others. Examples of substances secreted into the urine are hydrogen, ammonium, potassium and uric acid. In addition, the kidneys also carry out various other functions, such as hormone synthesis, and others.

A recessed area on the concave border of the kidney 70 is the renal hilum 81, where the renal artery 69 (not shown in the detailed view of the kidney 70) enters the kidney 70 and the renal vein 67 (not shown in detailed view) and ureter 63 leave. The kidney 70 is surrounded by tough fibrous tissue, the renal capsule 74, which is itself surrounded by perirenal fat, renal fascia, and pararenal fat. The anterior (front) surface of these tissues is the peritoneum, while the posterior (rear) surface is the transversalis fascia.

The functional substance, or parenchyma, of the kidney 70 is divided into two major structures: the outer renal cortex 77 and the inner renal medulla 87. These structures take the shape of a plurality of generally cone-shaped renal lobes, each containing renal cortex surrounding a portion of medulla called a renal pyramid 72. Between the renal pyramids 72 are projections of cortex called renal columns 73. Nephrons (not shown in detail in FIG. 1), the urine-producing functional structures of the kidney, span the cortex 77 and medulla 87. The initial filtering portion of a nephron is the renal corpuscle, which is located in the cortex and is followed by a renal tubule that passes from the cortex deep into the medullary pyramids. Part of the renal cortex, a medullary ray, is a collection of renal tubules that drain into a single collecting duct.

The tip/apex, or papilla 79, of each renal pyramid empties urine into a respective minor calyx 75; minor calyces 75 empty into major calyces 76, and major calyces 76 empty into the renal pelvis 71, which transitions to the ureter 63. The manifold-type collection of minor and major calyces may be referred to herein as the "calyx network" of the kidney. At the hilum 81, the ureter 63 and renal vein 67 exit the kidney and the renal artery 69 enters. Hilar fat and lymphatic tissue with lymph nodes surrounds these structures. The hilar fat is contiguous with a fat-filled cavity called the renal sinus. The renal sinus collectively contains the renal pelvis 71 and calyces 75, 76 and separates these structures from the renal medullary tissue. The funnel/tubular-shaped anatomy associated with the calyces can be referred to as the infundibulum/infundibula. That is, an infundibulum generally leads to the termination of a calyx where a papilla is exposed within the calyx.

With further reference to the medical system 100, the medical instrument 40 (e.g., scope, directly-entry instrument, etc.) can be advanced into the kidney 70 through the urinary tract. Specifically, a ureteral access sheath 90 may be disposed within the urinary tract to an area near the kidney 70. The medical instrument 40 may be passed through the ureteral access sheath 90 to gain access to the internal anatomy of the kidney 70, as shown. Once at the site of the kidney stone 80 (e.g., within a target calyx 75 of the kidney 70 through which the stone 80 is accessible), the medical instrument 40 can be used to channel/direct the basketing device 30 to the target location. Once the stone 80 has been captured in the distal basket portion 35 of the basketing device 30, the utilized ureteral access path may be used to extract the kidney stone 80 from the patient 7.

The system 100 may advantageously be configured to implement certain stuck-instrument detection/determination functionality as disclosed in detail herein. Such stuck-instrument detection/determination may advantageously provide for effective detection/determination of a stuck-instrument condition, user warning generation and/or provision regarding the stuck-instrument condition, and/or, in some instances, prevention or reduced risk of the occurrence of stuck medical instruments during retraction thereof. Stuck-instrument detection functionality in accordance with aspects of the present disclosure can advantageously provide a layer of safety with respect to at least partially robotic basketing implementation. For example, robotic-assisted stuck-instrument detection, as described in detail herein in connection with various embodiments, can provide an additional layer of stuck-instrument detection beyond the attention and judgment of the operating physician or technician, thereby providing improved safety conditions for the patient and/or reduce risk of instrument damage. Furthermore, compared to certain manual basketing solutions, systems/embodiments of the present disclosure providing enhanced stuck basket detection functionality based on instrumentation actuator force readings can allow for a user to operate a basketing device to safely retract a captured object/stone, wherein such solution requires only a single operator while providing the same or greater amount of protection against damage from a stuck-instrument condition, with both vision feedback and force feedback from the robotic system.

The various scope-type instruments disclosed herein, such as the scope 40 of the system 100, can be configured to navigate within the human anatomy, such as within a natural orifice or lumen of the human anatomy. The terms "scope" and "endoscope" are used herein according to their broad and ordinary meanings, and may refer to any type of elongate medical instrument having image generating, viewing, and/or capturing functionality and configured to be introduced into any type of organ, cavity, lumen, chamber, or space of a body. A scope can include, for example, a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), colonoscope (e.g., for accessing the colon and/or rectum), borescope, and so on. Scopes/endoscopes, in some instances, may comprise a rigid or flexible tube, and may be dimensioned to be passed within an outer sheath, catheter, introducer, or other lumen-type device, or may be used without such devices.

Figure 2:
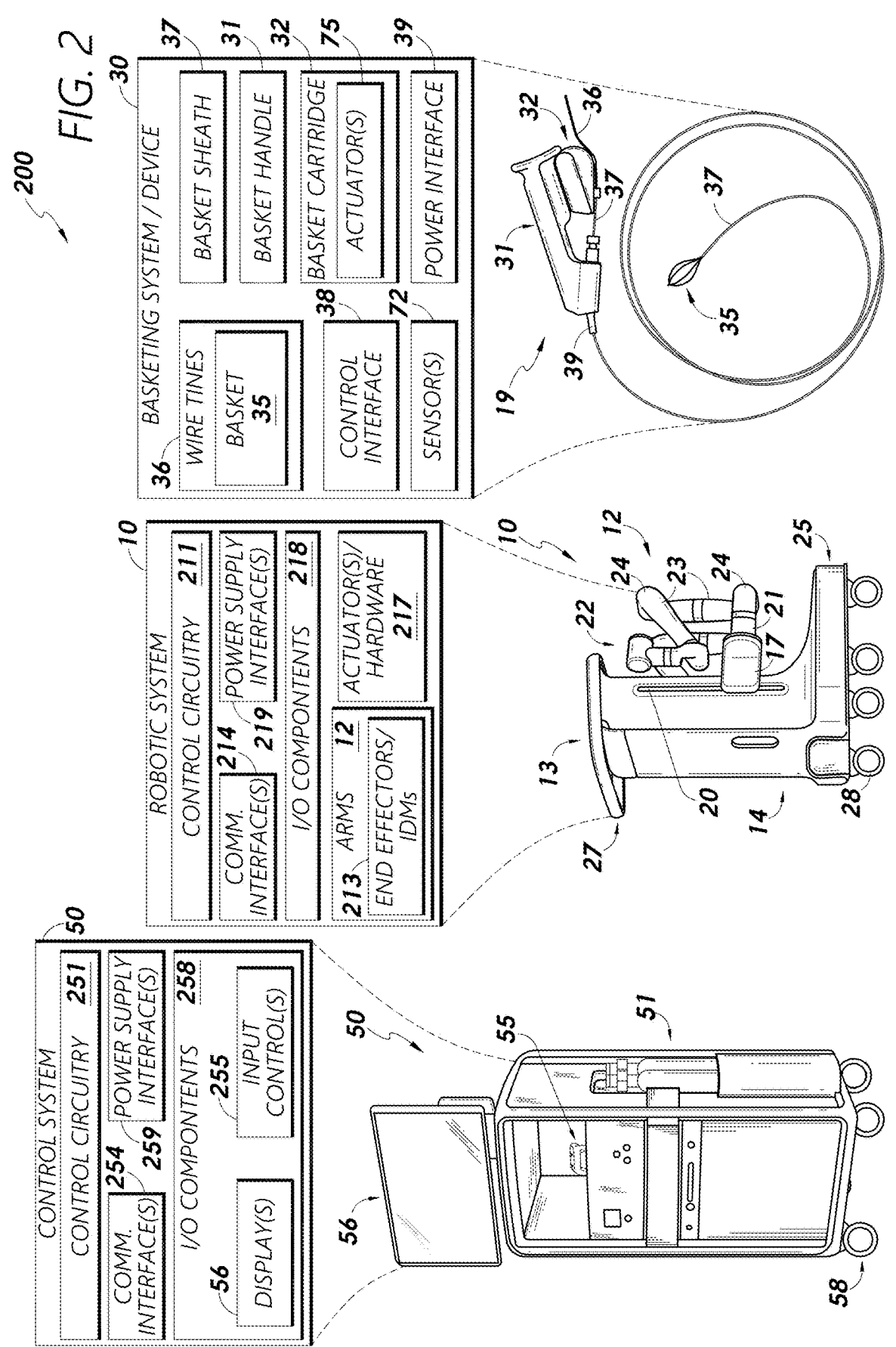
FIG. 2 illustrates medical system components that may be implemented in the medical system of FIG. 1 in accordance with one or more embodiments.

With reference to FIG. 1 and FIG. 2, which shows an example embodiment of the control system 50 of FIG. 1 in accordance with one or more embodiments of the present disclosure, the control system 50 can be configured to provide various functionality to assist in performing a medical procedure. In some embodiments, the control system 50 can be coupled to the robotic system 10 and operate in cooperation therewith to perform a medical procedure on the patient 7. For example, the control system 50 can communicate with the robotic system 10 via a wireless or wired connection (e.g., to control the robotic system 10). Further, in some embodiments, the control system 50 can communicate with the robotic system 10 to receive position data therefrom relating to the position of the distal end of the scope 40, access sheath 90, or basketing device 30. Such positional data relating to the position of the scope 40, access sheath 90, or basketing device 30 may be derived using one or more electromagnetic sensors associated with the respective components. Moreover, in some embodiments, the control system 50 can communicate with the table 15 to position the table 15 in a particular orientation or otherwise control the table 15. In some embodiments, the control system 50 can communicate with the EM field generator 18 to control generation of an EM field in an area around the patient 7.

FIG. 2 further shows an example embodiment of the robotic system 10 of FIG. 1 in accordance with one or more embodiments of the present disclosure. The robotic system 10 can be configured to at least partly facilitate execution of a medical procedure. The robotic system 10 can be arranged in a variety of ways depending on the particular procedure. The robotic system 10 can include one or more robotic arms 12 configured to engage with and/or control, for example, the scope 40 and/or the basketing system 30 to perform one or more aspects of a procedure. As shown, each robotic arm 12 can include multiple arm segments 23 coupled to joints 24, which can provide multiple degrees of movement/freedom. In the example of FIG. 1, the robotic system 10 is positioned proximate to the patient's legs and the robotic arms 12 are actuated to engage with and position the scope 40 for access into an access opening, such as the urethra 65 of the patient 7. When the robotic system 10 is properly positioned, the scope 40 can be inserted into the patient 7 robotically using the robotic arms 12, manually by the physician 5, or a combination thereof. A scope-driver instrument coupling 11 (i.e., instrument device manipulator (IDM)) can be attached to the distal portion of one of the arms 12b to facilitate robotic control/advancement of the scope 32. Another 12c of the arms may have associated therewith an instrument coupling/manipulator 19 that is configured to facilitate advancement and operation of the basketing device 30. The scope 40 may include one or more working channels through which additional tools, such as lithotripters, basketing devices, forceps, etc., can be introduced into the treatment site.

The robotic system 10 can be coupled to any component of the medical system 100, such as to the control system 50, the table 15, the EM field generator 18, the scope 40, the basketing system 30, and/or any type of percutaneous-access instrument (e.g., needle, catheter, nephroscope, ect.). In some embodiments, the robotic system 10 is communicatively coupled to the control system 50. For example, the robotic system 10 may be configured to receive control signals from the control system 50 to perform certain operations, such as to position one or more of the robotic arms 12 in a particular manner, manipulate the scope 40, manipulate the basketing system 30, and so on. In response, the robotic system 10 can control, using certain control circuitry 211, actuators 217, and/or other components of the robotic system 10, a component of the robotic system 10 to perform the operations. In some embodiments, the robotic system 10 and/or control system 50 is/are configured to receive images and/or image data from the scope 40 representing internal anatomy of the patient 7, namely the urinary system with respect to the particular depiction of FIG. 1, and/or display images based thereon.

With reference to FIG. 2, the robotic system 10 generally includes an elongated support structure 14 (also referred to as a "column"), a robotic system base 25, and a console 13 at the top of the column 14. The column 14 may include one or more arm supports 17 (also referred to as a "carriage") for supporting the deployment of the one or more robotic arms 12 (three shown in FIG. 2). The arm support 17 may include individually-configurable arm mounts that rotate along a perpendicular axis to adjust the base of the robotic arms 12 for desired positioning relative to the patient.

The arm support 17 may be configured to vertically translate along the column 14. In some embodiments, the arm support 17 can be connected to the column 14 through slots 20 that are positioned on opposite sides of the column 14 to guide the vertical translation of the arm support 17. The slot 20 contains a vertical translation interface to position and hold the arm support 17 at various vertical heights relative to the robotic system base 25. Vertical translation of the arm support 17 allows the robotic system 10 to adjust the reach of the robotic arms 12 to meet a variety of table heights, patient sizes, and physician preferences. Similarly, the individually-configurable arm mounts on the arm support 17 can allow the robotic arm base 21 of robotic arms 12 to be angled in a variety of configurations.

The robotic arms 12 may generally comprise robotic arm bases 21 and end effectors 22, separated by a series of linking arm segments 23 that are connected by a series of joints 24, each joint comprising one or more independent actuators 217. Each actuator may comprise an independently-controllable motor. Each independently-controllable joint 24 can provide or represent an independent degree of freedom available to the robotic arm. In some embodiments, each of the arms 12 has seven joints, and thus provides seven degrees of freedom, including "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The robotic system base 25 balances the weight of the column 14, arm support 17, and arms 12 over the floor. Accordingly, the robotic system base 25 may house certain relatively heavier components, such as electronics, motors, power supply, as well as components that selectively enable movement or immobilize the robotic system. For example, the robotic system base 25 can include wheel-shaped casters 28 that allow for the robotic system to easily move around the operating room prior to a procedure. After reaching the appropriate position, the casters 28 may be immobilized using wheel locks to hold the robotic system 10 in place during the procedure.

Positioned at the upper end of column 14, the console 13 can provide both a user interface for receiving user input and a display screen 16 (or a dual-purpose device such as, for example, a touchscreen) to provide the physician/user with both pre-operative and intra-operative data. Potential pre-operative data on the console/display 16 or display 56 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 13 may be positioned and tilted to allow a physician to access the console from the side of the column 14 opposite arm support 17. From this position, the physician may view the console 13, robotic arms 12, and patient while operating the console 13 from behind the robotic system 10. As shown, the console 13 can also include a handle 27 to assist with maneuvering and stabilizing robotic system 10.

The end effector 213 of each of the robotic arms 12 may comprise, or be configured to have coupled thereto, an instrument device manipulator (IDM), which may be attached using a mechanism changer interface (MCI). In some embodiments, the IDM can be removed and replaced with a different type of IDM, for example, a first type 11 of IDM may manipulate an endoscope, while a second type 19 of IDM may manipulate a basketing device. Another type of IDM may be configured to hold an electromagnetic field generator 18. An MCI can provide power and control interfaces. For example, the interfaces can include connectors to transfer pneumatic pressure, electrical power, electrical signals, and/or optical signals from the robotic arm 12 to the IDM. The IDMs 213 may be configured to manipulate medical instruments (e.g., surgical tools/instruments), such as the scope 40, using techniques including, for example, direct drives, harmonic drives, geared drives, belts and pulleys, magnetic drives, and the like. In some embodiments, the medical device manipulators 213 can be attached to respective ones of the robotic arms 212, wherein the robotic arms 212 are configured to insert or retract the respective coupled medical instruments into or out of the treatment site.

As referenced above, the system 100 can include certain control circuitry configured to perform certain of the functionality described herein, including the control circuitry 211 of the robotic system 10 and the control circuitry 251 of the control system 50. That is, the control circuitry of the system 100 may be part of the robotic system 10, the control system 50, or some combination thereof. Therefore, any reference herein to control circuitry may refer to circuitry embodied in a robotic system, a control system, or any other component of a medical system, such as the medical system 100 shown in FIG. 1. The term "control circuitry" is used herein according to its broad and ordinary meaning, and may refer to any collection of processors, processing circuitry, processing modules/units, chips, dies (e.g., semiconductor dies including come or more active and/or passive devices and/or connectivity circuitry), microprocessors, micro-controllers, digital signal processors, microcomputers, central processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry referenced herein may further include one or more circuit substrates (e.g., printed circuit boards), conductive traces and vias, and/or mounting pads, connectors, and/or components. Control circuitry referenced herein may further comprise one or more storage devices, which may be embodied in a single memory device, a plurality of memory devices, and/or embedded circuitry of a device. Such data storage may comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware and/or software state machine, analog circuitry, digital circuitry, and/or logic circuitry, data storage device (s)/register(s) storing any associated operational instructions may be embedded within, or external to, the circuitry comprising the state machine, analog circuitry, digital circuitry, and/or logic circuitry.

The control circuitry 211, 251 may comprise computer-readable media storing, and/or configured to store, hard-coded and/or operational instructions corresponding to at least some of the steps and/or functions illustrated in one or more of the present figures and/or described herein. Such computer-readable media can be included in an article of manufacture in some instances. The control circuitry 211/251 may be entirely locally maintained/disposed or may be remotely located at least in part (e.g., communicatively coupled indirectly via a local area network and/or a wide area network). Any of the control circuitry 211, 251 may be configured to perform any aspect(s) of the various processes disclosed herein, including the processes shown in FIGS. 9 and 11, as described below.

With respect to the robotic system 10, at least a portion of the control circuitry 211 may be integrated with the base 25, column 14, and/or console 13 of the robotic system 10, and/or another system communicatively coupled to the robotic system 10. With respect to the control system 50, at least a portion of the control circuitry 251 may be integrated with the console base 51 and/or display unit 56 of the control system 50. It should be understood that any description herein of functional control circuitry or associated functionality may be understood to be embodied in the robotic system 10, the control system 50, or any combination thereof, and/or at least in part in one or more other local or remote systems/devices.

With further reference to FIG. 2, the control system 50 can include various I/O components 258 configured to assist the physician 5 or others in performing a medical procedure. For example, the input/output (I/O) components 258 can be configured to allow for user input to control/navigate the scope 40 and/or basketing system within the patient 7. In some embodiments, for example, the physician 5 can provide input to the control system 50 and/or robotic system 10, wherein in response to such input, control signals can be sent to the robotic system 10 to manipulate the scope 40 and/or catheter basketing system 30. The control system 50 can include one or more display devices 56 to provide various information regarding a procedure. For example, the display (s) 56 can provide information regarding the scope 40 and/or basketing system 30. For example, the control system 50 can receive real-time images that are captured by the scope 40 and display the real-time images via the display(s) 56. Additionally or alternatively, the control system 50 can receive signals (e.g., analog, digital, electrical, acoustic/sonic, pneumatic, tactile, hydraulic, etc.) from a medical monitor and/or a sensor associated with the patient 7, and the display(s) 56 can present information regarding the health or environment of the patient 7. Such information can include information that is displayed via a medical monitor including, for example, information relating to heart rate (e.g., ECG, HRV, etc.), blood pressure/rate, muscle bio-signals (e.g., EMG), body temperature, blood oxygen saturation (e.g., $SpO_2$), $CO_2$, brainwaves (e.g., EEG), environmental and/or local or core body temperature, and so on.

To facilitate the functionality of the control system 50, the control system can include various components (sometimes referred to as "subsystems"). For example, the control system 50 can include the control electronics/circuitry 251, as well as one or more power supplies/supply interfaces 259, pneumatic devices, optical sources, actuators, data storage devices, and/or communication interfaces 254. In some embodiments, the control system 50 is movable, while in other embodiments, the control system 50 is a substantially stationary system. Although various functionality and components are discussed as being implemented by the control system 50, any of such functionality and/or components can be integrated into and/or performed by other systems and/or devices, such as the robotic system 10, the basketing system 30, the table 15, and/or others, for example.

With further reference to FIG. 1, the medical system 100 can provide a variety of benefits, such as providing guidance to assist a physician in performing a procedure (e.g., instrument tracking, instrument alignment information, etc.), enabling a physician to perform a procedure from an ergonomic position without the need for awkward arm motions and/or positions, enabling a single physician to perform a procedure with one or more medical instruments, avoiding radiation exposure (e.g., associated with fluoroscopy techniques), enabling a procedure to be performed in a single operative setting, providing continuous suction to remove an object more efficiently (e.g., to remove a kidney stone), and so on. For example, the medical system 100 can provide guidance information to assist a physician in using various medical instruments to access a target anatomical feature while minimizing bleeding and/or damage to anatomy (e.g., critical organs, blood vessels, etc.). Further, the medical system 100 can provide non-radiation-based navigational and/or localization techniques to reduce physician and patient exposure to radiation and/or reduce the amount of equipment in the operating room. Moreover, the medical system 100 can provide functionality that is distributed between the control system 50 and the robotic system 10, which may be independently movable. Such distribution of functionality and/or mobility can enable the control system 50 and/or the robotic system 10 to be placed at locations that are optimal for a particular medical procedure, which can maximize working area around the patient 7 and/or provide an optimized location for the physician 5 to perform a procedure.

The various components of the system 100 can be communicatively coupled to each other over a network, which can include a wireless and/or wired network. Example networks include one or more personal area networks (PANs), local area networks (LANs), wide area networks (WANs), Internet area networks (LANs), cellular networks, the Internet, personal area networks (PANs), body area network (BANs), etc. For example, the various communication interfaces of the systems of FIG. 2 can be configured to communicate with one or more device/sensors/systems, such as over a wireless and/or wired network connection. In some embodiments, the various communication interfaces can implement a wireless technology such as Bluetooth, Wi-Fi, near field communication (NFC), or the like. Furthermore, in some embodiments, the various components of the system 100 can be connected for data communication, fluid exchange, power exchange, and so on via one or more support cables, tubes, or the like.

The control system 50, basking system 30, and/or robotic system 10 can include certain user controls (e.g., controls 55), which may comprise any type of user input (and/or output) devices or device interfaces, such as one or more buttons, keys, joysticks, handheld controllers (e.g., video-game-type controllers), computer mice, trackpads, trackballs, control pads, and/or sensors (e.g., motion sensors or cameras) that capture hand gestures and finger gestures, touchscreens, and/or interfaces/connectors therefore. Such user controls are communicatively and/or physically coupled to respective control circuitry.

In some embodiments, a user can manually manipulate a robotic arm 12 of the robotic system 10 without using electronic user controls. For example, during setup in a surgical operating room, a user may move the robotic arms 12 and/or any other medical instruments to provide desired access to a patient. The robotic system 10 may rely on force feedback and inertia control from the user to determine appropriate configuration of the robotic arms 12 and associated instrumentation.

The basketing system 30 comprises various hardware and control components. For example, as shown in FIG. 2, the processing system 30 can comprise a basket 35 formed of one or more wire tines 36. For example, the basketing system 30 may comprise four wire tines disposed within a basketing sheath 37 over a length thereof, wherein the tines project from a distal end of the sheath 37 to form the basket form 35. The tines 36 further extend from the proximal end of the sheath 37. The tines 36 may be configured to be slidable within the basketing sheath 37, subject to some amount of frictional resistance. The tines 36 and the sheath 37 can be coupled to respective actuators 75 of a basket cartridge component 32. The relationship between the actuators 75 of the basket cartridge 32 and the tines 36 and sheath 37 is described in detail below with respect to FIGS. 4A-4E. The basket cartridge 32 may be physically and/or communicatively coupled to a handle portion/component 31 of the basketing system 30. The handle component 31 can be configured to be used to assist in basketing control either manually or through robotic control.

The basketing system 30 can be powered through a power interface 39 and/or controlled through a control interface 38, each or both of which may interface with a robotic arm/component of the robotic system 10. The basketing system 30 may further comprise one or more sensors 72, such as pressure and/or other force-reading sensors, which may be configured to generate signals indicating forces experienced at/by one or more of the actuators 75 and/or other couplings of the basketing system 30. Such sensor readings may be used to determine stuck basket conditions, as described in detail herein. In some embodiments, the sensor(s) 72 include one or more sensors configured to directly measure forces are at or near the basket portion 35 of the tines 36. For example, a force sensor on the tip of the basket 35 and/or at a tip of an access sheath through which the basketing device 30 accesses the target anatomy can be used to directly detect forces on the basket 35 that result from the basket 35 becoming stuck on anatomy or on an opening at an end of the access sheath.

Basketing Control

Figure 3:
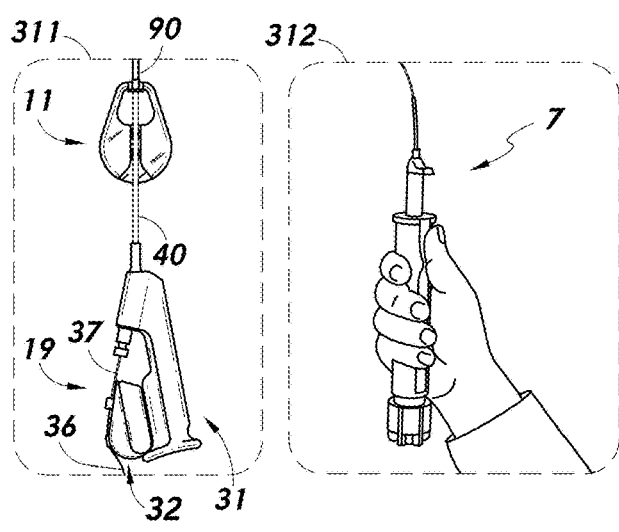
FIG. 3 illustrates a ureteroscope including a basketing device in a working channel thereof disposed in portions of the urinary system of a patient in accordance with one or more embodiments.

FIG. 3 illustrates a ureteroscope 40 disposed in portions of the urinary system of a patient in accordance with one or more embodiments of the present disclosure. As referenced above, ureteroscopic procedures can be implemented for investigating abnormalities in human ureters and/or treating the same. For example, ureteroscope procedures can be implemented to treat and/or remove kidney stones. Such procedures may be implemented manually at least in part and/or may be performed using robotic technologies at least in part, such as the robotic system 10 shown in FIG. 1. For example, use of robotic devices and/or systems for certain endoscopic procedures can provide relatively greater precision, control, and/or coordination compared to strictly manual procedures. In some embodiments, the scope 40 includes a working channel 44 for deploying a basketing device 30 (e.g., basket component 35) to an operative region at a distal end of the scope.

The access sheath 90 through which the scope 40 is passed to access the target anatomy can advantageously have a diameter sufficient to have the scope 40 drawn therethrough, in addition to an object captured in the basket 35 when the object/stone is not too large in size. The access sheath 90 may be advanced through the ureter 63 to a position near the renal pelvis 71 and/or ureteropelvic junction 71. The distal end of the access sheath 90 may be parked at a position in the ureter 63 and/or renal pelvis 71, wherein such parking position may be at least partially anatomy-dependent. That is, the access sheath 90 may be placed as far into the renal anatomy as possible, as permitted by the urinary tract path, which may be somewhat tortuous in certain portions thereof. Generally, the access sheath 90 may not be articulable to the degree that the scope 40 can be articulated, and therefore it may not be practical to navigate/drive the access sheath 90 into the kidney.

The scope 40 can be articulable, such as with respect to at least a distal portion of the scope, so that the scope can be steered within the human anatomy. In some embodiments, the scope 40 is configured to be articulated with, for example, five degrees of freedom, including XYZ coordinate movement, as well as pitch and yaw. In some embodiments, the scope 40 is articulatable with six degrees of freedom, including XYZ coordinate movement, as well as pitch, yaw, and roll. Position sensor(s) (e.g., electromagnetic sensors) of the scope 40 may likewise have similar degrees of freedom with respect to the position information they produce/provide.

For robotic implementations, robotic arms of a robotic system can be configured/configurable to manipulate the scope 40 using elongate movement members. The elongate movement members may include one or more pull wires (e.g., pull or push wires), cables, fibers, and/or flexible shafts. For example, the robotic arms may be configured to actuate multiple pull wires (not shown) coupled to the scope 40 to deflect the tip 42 of the scope 40. Pull wires may include any suitable or desirable materials, such as metallic and non-metallic materials such as stainless steel, Kevlar, tungsten, carbon fiber, and the like. In some embodiments, the scope 40 is configured to exhibit nonlinear behavior in response to forces applied by the elongate movement members. The nonlinear behavior may be based on stiffness and compressibility of the scope, as well as variability in slack or stiffness between different elongate movement members.

The scope (e.g., endoscope/ureteroscope) 40 may comprise a tubular and flexible medical instrument that is configured to be inserted into the anatomy of a patient to capture images of the anatomy. In some embodiments, the scope 40 can accommodate wires and/or optical fibers to transfer signals to/from an optical assembly and a distal end 42 of the scope 40, which can include an imaging device 48, such as an optical camera. The scope 40 can further include a light source 49, such as an LED or fiber-optic light source/lens.

The camera/imaging device 48 can be used to capture images of an internal anatomical space, such as internal calyces of the kidney 70. The scope 40 may further be configured to accommodate optical fibers to carry light from proximately-located light sources, such as light-emitting diodes, to the distal end 42 of the scope. The distal end 42 of the scope 40 can include ports for light sources to illuminate an anatomical space when using the camera/imaging device. In some embodiments, the scope 40 is configured to be controlled by a robotic system similar in one or more respects to the robotic system 10 shown in FIGS. 1 and 2. The imaging device 48 may comprise an optical fiber, fiber array, and/or lens. The optical components move along with the tip of the scope 40 such that movement of the tip of the scope results in changes to the images captured by the imaging device(s) 48.

In some embodiments, the medical instrument (e.g., scope) 40 includes a sensor that is configured to generate and/or send sensor position data to another device or produce a detectable distortion or signature in an electromagnetic field. The sensor position data can indicate a position and/or orientation of the medical instrument 40 (e.g., the distal end 42 thereof) and/or can be used to determine/infer a position/orientation of the medical instrument. For example, a sensor (sometimes referred to as a "position sensor") can include an electromagnetic (EM) sensor with a coil of conductive material or other form/embodiment of an antenna. In some embodiments, the scope 40 comprises an electromagnetic sensor that is potted in the distal end 42 of the scope 40. The electromagnetic sensor (not shown) may comprise a termination of a wire, or other conductive element, configured to induce electrical currents in the presence of an electromagnetic field. Further, the medical instrument/scope 40 and/or basketing device 30 can include other types of sensors, such as a shape sensing fiber, accelerometer(s), gyroscope(s), satellite-based positioning sensor(s) (e.g., global positioning system (GPS) sensors), radio-frequency transceiver(s), and so on. In some embodiments, a sensor on a medical instrument can provide sensor data to a control system, which is then used to determine a position and/or an orientation of the medical instrument. Position data derived using one or more position sensors associated with the scope 40 or basketing device 30 can be used to determine when the scope and/or basket 35 is within or near to a stuck instrument hazard zone, as described in detail herein.

The scope 40 and/or basketing device 30 may be controllable in any suitable or desirable way, either based on manual manipulation of handle component(s), electronic user input, or automatically. For example, the image 311 shows an example robotic control configuration for controlling the scope 40 and/or basketing device 30, whereas the image 312 shows an example manual control configuration. In some embodiments, the scope 40 and/or basketing device 30 can be controlled using a two-handed controller 55, as shown in FIG. 1. Although the controller 55 is shown as handheld controller, user input may be received using any type of I/O device, such as a touchscreen/pad, a mouse, a keyboard, a microphone, etc.

FIGS. 4A-4D illustrate a basketing control system in various configurations in accordance with one or more embodiments. In connection with the various embodiments of the present disclosure, basketing may be performed at least in part using one or more robotic instrument device manipulators (IDMs), such as a scope-driver IDM 11 and a basketing IDM 19, as shown in FIGS. 4A-4D. The IDMs 11, 19 may be coupled to one or more robotic arms of a robotic system. Control signals for controlling the various actuators associated with the IDMs 11, 19 may be provided using control interfaces between the IDMs and respective robotic arms coupled thereto.

In some embodiments, the basketing IDM 19 can include a handle component 31 and a basketing cartridge component 32. The handle component 31 may be coupled to the scope 40 at a proximal end of the scope, and may include a channel through which a basketing device sheath 37 may enter the scope 40, wherein the basketing sheath 37 (along with basketing tines disposed there) may be disposed at least partially within a working channel 44 of the scope 40, as described above with respect to FIG. 3. The scope 40 and the basketing device 30 may generally be in a relatively fixed position at the handle component 31, wherein the relative position between the scope 40 and the basket 30 may be changed through actuation of one or more of the actuators 33, 34 of the basketing cartridge 32. Actuation of the basketing sheath actuator 33 can cause insertion and retraction of the basketing device 30 relative to the scope 40.

In some embodiments, some implementations of scope and/or basket retraction processes, the basketing device 30 may be dithered with respect to the scope 40 for various purposed, including improving stuck-instrument detection sensitivity and/or preventing instrument sticking. Dithering motion of the basketing device 30, as described in detail below in connection with various stuck-instrument detection solutions disclosed herein, may be implemented at least in part by sliding the basketing sheath actuator 33 back-and-forth (e.g., distally and proximally) in an oscillating manner, such that the basket 35 moves back-and-forth relative to the distal end of the scope 40.

Figures 4A, 4B:
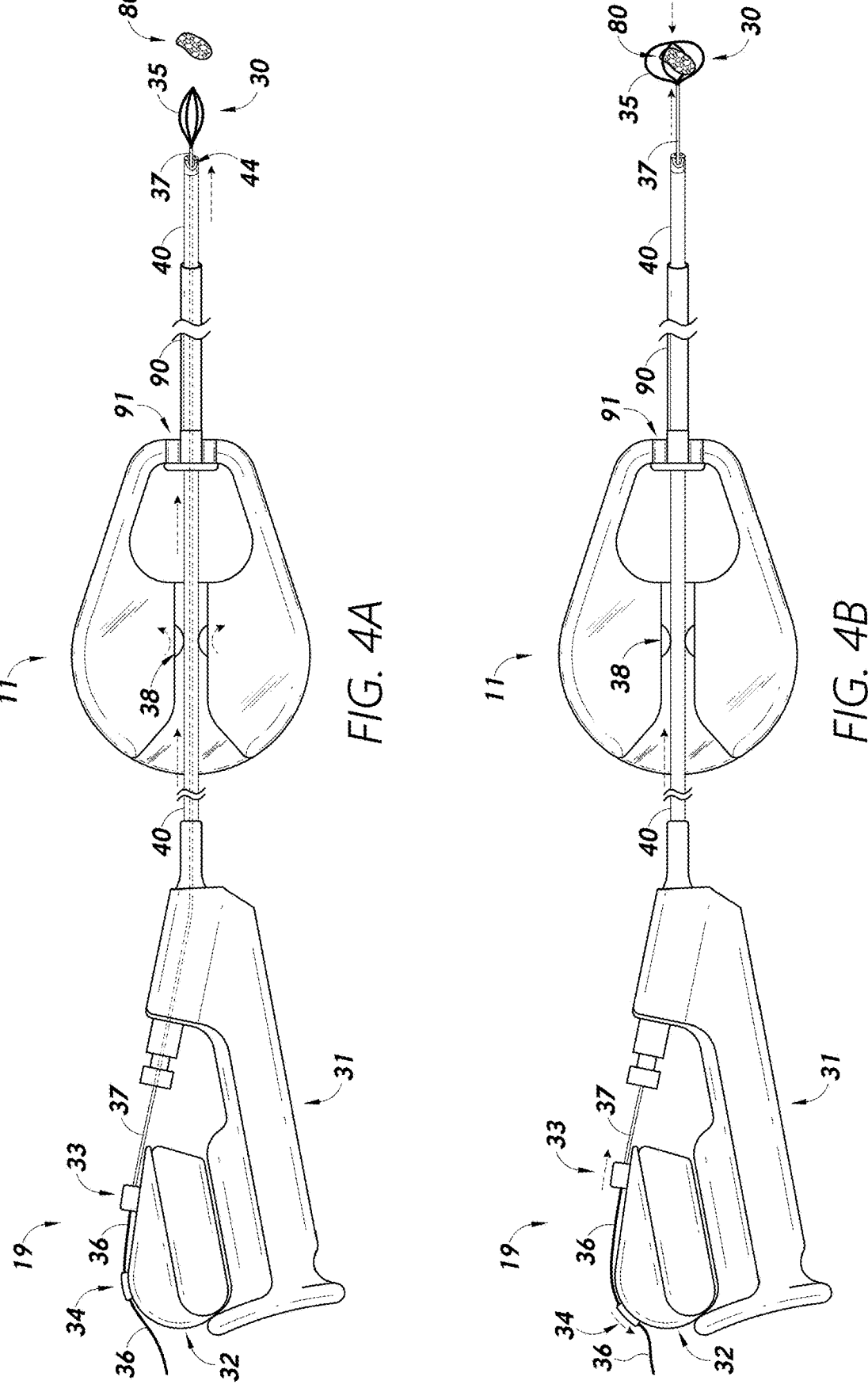
FIGS. 4A-4E illustrate a basketing system in various configurations in accordance with one or more embodiments.

The scope 40 may be advanced from the distal end of the access sheath 90 by driving one or more actuators 38 associated with the scope-driver IDM 11. For example, such actuators 38 may comprise wheel-type actuators, or the like. The actuators 38 may be used to advance and retract the scope 40. During a kidney stone removal procedure, the actuators 38 may be utilized to retract the scope 40 following successful capture of a kidney stone 80 in the basket 35, as shown in FIG. 4E. In some embodiments, the access sheath 90 is coupled to the scope-driver IDM 11 in a fixed manner using a sheath coupling component 91.

The basketing cartridge 32 may comprise a plurality of actuators 33, 34. For example, the actuators 33, 34 may comprise sliding, carriage-type actuators. Specifically, the cartridge 32 may include a first actuator 33 that is fixed to the sheath component 37 of the basketing device 30, as well as a second actuator 34 that is fixed to the wires/tines 36 of the basketing device 30, wherein the tines 36 may pass through and/or otherwise be disposed at least partially within the basketing sheath 37. In some embodiments, the basket 35 is formed of the tines 36 at a distal portion thereof that projects out of the distal end of the basketing sheath 37.

By sliding the sheath actuator 33, the basketing device 30 can be projected from the distal end of the scope 40. For example, as shown in FIG. 4B, the actuator 30 may be slid forward to produce a corresponding forward advancement of the basketing device 30 and basket 35. The basket actuator 34 can be used to open the basket 35 by pulling the tines proximally, thereby causing the distal end 39 of the basket 35 to be pulled toward the distal opening of the sheath 37, thereby resulting in outward bowing/expansion of the basket portion 35 of the tines. With the tines 35 in the expanded/open position shown in FIG. 4B, the basket 35 may be placed around a stone/object 80 to thereby capture the stone/object 80 within the basket tines 35.

Figures 4C, 4D:
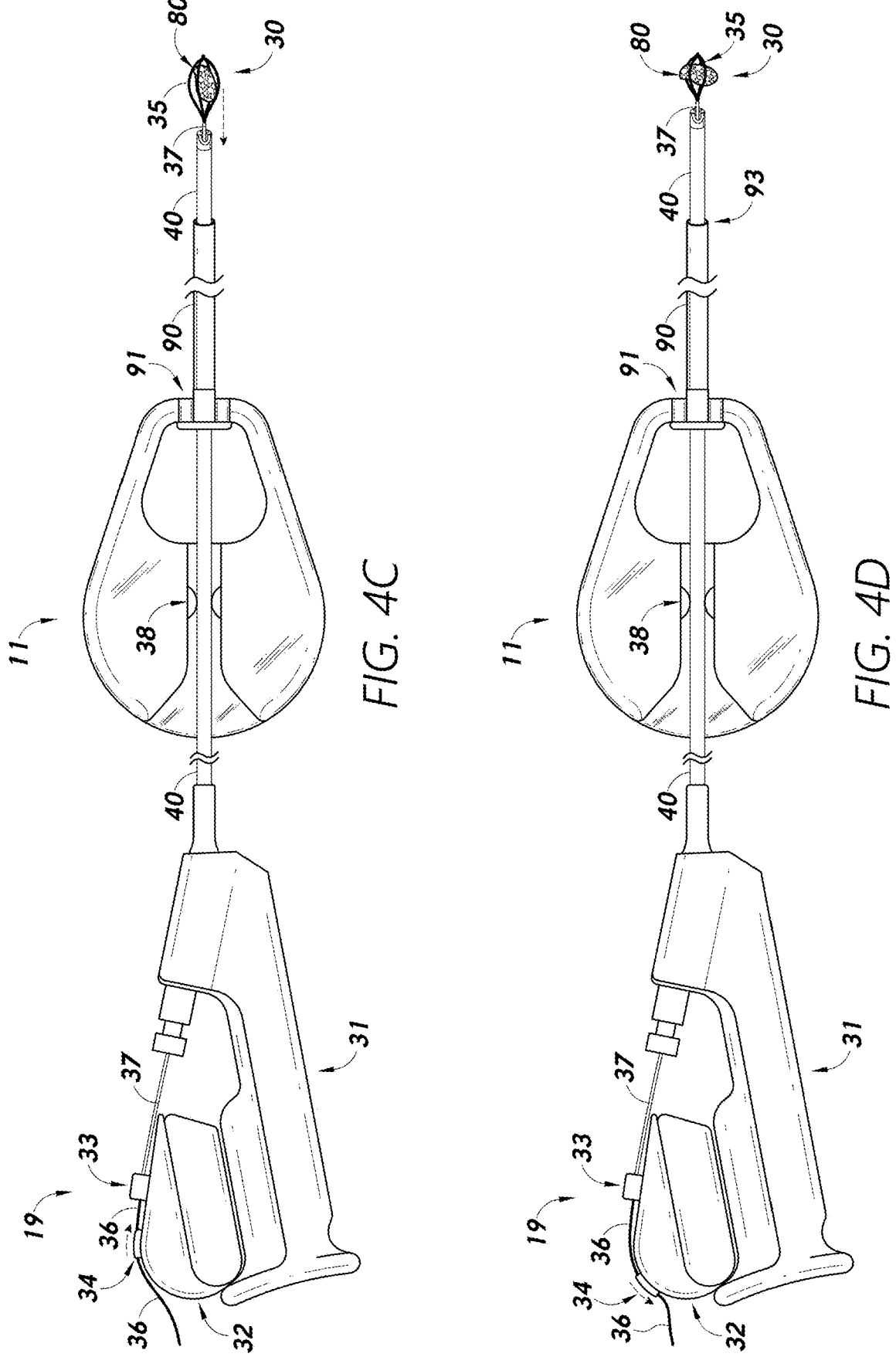
Figure 4E:
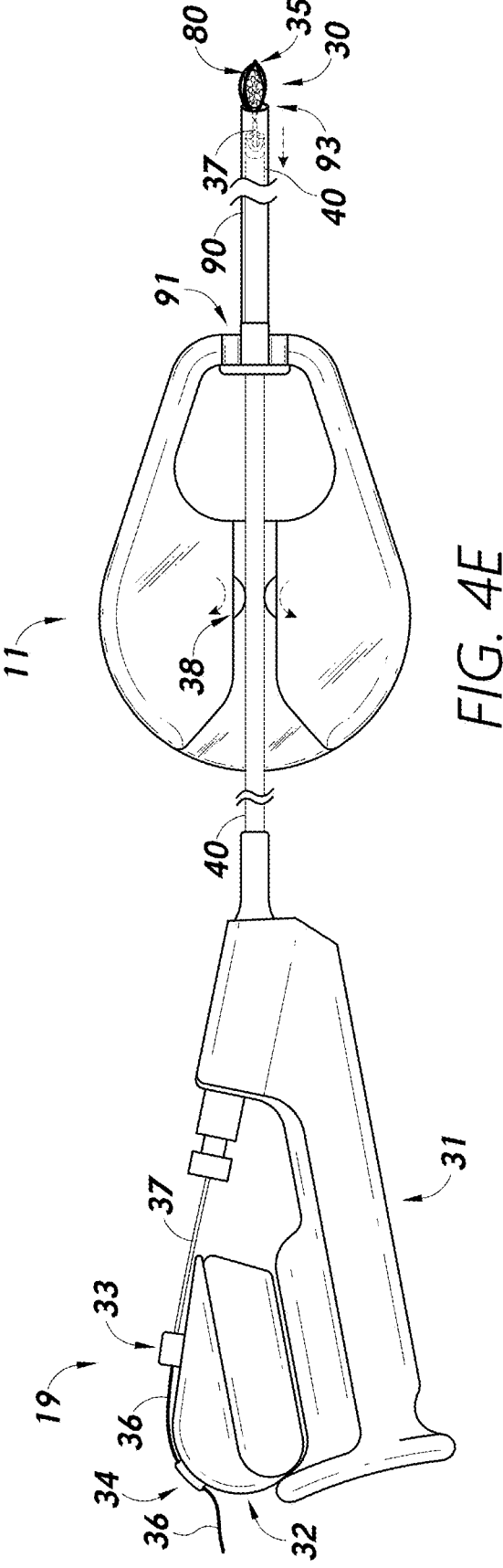

As shown in FIG. 4C, the basket 35 may be collapsed around the stone 80 to thereby capture the stone therein. For example, the basket tine actuator 34 may be advanced some amounts relative to the sheath actuator 33 to thereby push the basket tines farther out of the sheath 37 at a distal end thereof, thereby elongating/extending the basket 35 and bringing the tines closer to an axis of the basketing device 30. The sheath actuator 33 may be drawn proximally to bring the basketing device 30 back closer to the distal end of the scope 40. For example, it may be desirable to have the basket 35 disposed proximal/adjacent to the distal end of the scope 40 during retraction of the scope and basketing device 30.

In some implementations, the basket 35 may be further cinched/collapsed around the stone 80 by drawing the tines 36 further proximally, to thereby draw the tines 35 farther into the sheath 37 and reduce the length of the tines that project distally from the distal end of the basketing sheath 37. FIG. 4D shows the basket 35 with a reduced size resulting from proximally moving the actuator 34 relative to the actuator 33.

Once the stone 80 is captured and the basket 35 is brought to the desired position near the distal end of the scope 40, the actuator(s) 38 may be engaged to retract the scope 40 through the opening 93 of the access sheath 90, and further through the access sheath 90, as shown in FIG. 4E. In some embodiments, the basketing device 30 may be retracted along with the scope 40 as the scope 40 is proximally drawn. For example, frictional forces between the basketing sheath 37 and the working channel 44 of the scope 40 may be such as to cause the basketing device 30 to accompany the scope 40 when the latter is retracted/moved.

One or more force sensors may be associated with one or more of the actuators and/or coupling interfaces of the basketing system shown in FIGS. 40A-40E. For example, force sensors (e.g. pressure sensors) may be associated with one or more of the basket tine actuator 34, basket sheath actuator 33, the scope-driver actuator(s) 38, and/or access sheath coupling 91. For example, in some embodiments, forces present and/or sensed at the basket tine actuator 34 may indicate a stuck-instrument condition wherein the basket tines 35 are caught and/or pull distally on the actuator 34 during retraction of the scope 40. In some embodiments, force readings at the basketing sheath actuator 33 may indicate stuck-instrument conditions. For example, when the basket tines 35 are pulled against the distal opening of the basket sheath 37 and/or along one or more portions thereof, such force/friction may be manifested at least in part at the sheath actuator 33. Therefore, embodiments of the present disclosure can involve evaluating/analyzing sensor readings associated with the basketing sheath actuator 33 to determine/identify a stuck-instrument condition. Generally, movement of the sheath actuator 33 causes the basketing sheath 37 and tines 36 to move in tandem.

In some embodiments, sensors associated with the scope-driver actuators 38 can provide signals indicating a stuck-instrument condition. For example, with the basket 35 stuck on anatomy or at the opening of the access sheath 90, retraction of the scope can be inhibited due to the friction between the basketing device 30 and the working channel 44 of the scope 40. For example, in some embodiments, the basketing device 30 may be clamped or otherwise fixed to one or more portions of the scope 40, such as at or near a portion of the handle component 31. Therefore, forces associated with a stuck basket can be felt and/or read at the actuators 38 that are coupled to the scope 40. In some embodiments, the force experienced by the access sheath 90, which may be felt/sensed at least in part at the sheath coupling 91, can provide an indication of a stuck-instrument condition. It should be understood that any of the embodiments disclosed herein may be implemented to determine stuck-instrument conditions based on sensor readings associated with the basket tine actuator 34, the basket sheath actuator 33, the scope driver actuator(s) 38, and/or the sheath coupling 91, or any combination thereof.

In some embodiments, the basket portion 35 of the tines 36 of the basketing device 30 may have associated therewith one or more force sensors, such as at a distal end 39 of the basket 35. Such a sensor may provide signals with reduced friction losses relative to signals experienced/generated at more proximal components/positions associated with the other actuators/couplings of the basketing system. Therefore, embodiments of the present disclosure that implement force sensors associated with distal basket portions 35 of the basketing device 30 can provide relatively sensitive readings indicating stuck-instrument conditions. In some embodiments, one or more force sensors may be disposed at a base of the basket 35 at or near the distal opening of the basketing sheath 37. Such sensor(s) may provide readings that may serve as a basis for stuck-instrument determinations in accordance with embodiments of the present disclosure.

Figure 5:
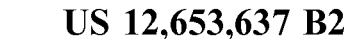
FIG. 5 illustrates various medical instruments, including certain basketing device components, disposed in portions of the renal anatomy of a patient in accordance with one or more embodiments.

FIG. 5 illustrates various medical instruments, including certain basketing device components, disposed in portions of the renal anatomy of a patient in accordance with one or more embodiments. In particular, FIG. 5 shows a scope 40 and basketing device 30 at various positions associated with a stone/object capture and removal procedure in accordance with aspects of the present disclosure.

As referenced above, attempting to extract a relatively large stone can result in tearing or other damage to the ureter and/or other anatomical feature(s). With respect to the diagram of FIG. 5, in cases where a stone 80 is too large to fit within the access sheath 90 (e.g., ureteral access sheath), thereby causing the basket 35c to become caught at the distal end or other portion of the access sheath 90, extraction forces on the scope 40 and/or basket device 30 can cause the access sheath 90 to move, possibly resulting in abrasion on the inner wall of ureter 63. Furthermore, if the basket 35 is attempted to be pulled within the access sheath 90 in a situation in which the basket does not fit cleanly therein due to the size of the stone 80 captured in the basket 35, the basket tines 35 can be damaged or broken.

In situations in which the targeted stone/object 80 is too large to be retracted cleanly through the ureteropelvic junction 78 and into the access sheath 90 for various reasons, embodiments of the present disclosure can provide effective solutions for detecting stuck-instrument conditions, or risks or instrument sticking/catching. As an example use case, when a target stone/object is broken (e.g., using a laser as part of a lithotripsy procedure), the operating physician may not be able to confidently determine the exact size or diameter of the stone and/or whether or not the stone/fragment is small enough to pass through the ureter and/or ureteral access sheath. According to some manual procedures, the physician may attempt to lase a stone/object to produce stone fragments small enough to fit cleanly through the ureteropelvic junction 78 and access sheath 90 based on personal experience with respect to such procedures. Nevertheless, such physicians may encounter stuck-instrument conditions during procedures over time. For manual procedures, when encountering a stuck-instrument condition, the physician holding the ureteroscope and monitoring real-time scope camera images may be able to identify/notice on camera that the stone/basket appears further away from the scope camera view than expected, which may be due to the basket/stone having become stuck on certain anatomy and/or at the opening of the access sheath 90. Furthermore, where the basket control is manually operated as well, a stuck instrument/stone condition may be tactually felt on the control instrument in the form of force opposing the retraction of the scope and/or basket.

As referenced above, the size of the stone 80 with respect to one or more dimensions thereof can cause the stone 80 to become stuck in the patient anatomy and/or at the opening of the access sheath 90 into which the scope 40, basket 35, and object 80 captured in the basket are drawn. However, according to certain solutions, it may not be possible for the position and/or system to determine the exact size of the stone 80. Therefore, risks of instrument sticking/catching may not be entirely avoidable in some cases. Furthermore, with respect to robotic-assisted ureteroscopic procedures, although camera views from endoscope cameras may be available for monitoring by the physician/technician, where the scope and/or basket device is robotically controlled rather than being held by a human surgical staff member, force feedback may not be felt by a human user. Therefore, detection/determination of stuck instrument/stone conditions can be more difficult in certain respects with respect to robotically-implemented scope-driving and/or basketing procedures.

In instances in which the stone 80 and/or the basket 35 become stuck in the patient anatomy, further retraction of the basket 35 from the stuck position can result in tissue tearing (e.g., ureter tearing). Furthermore, where the basket 35c becomes stuck at the opening of the access sheath 90, further retraction of the basket 35c and/or scope 40c can result in movement/dislodging of the access sheath 90 from its parked position, and/or damage to the basket 35.

Embodiments of the present disclosure provide for stuck-instrument detection based on force readings associated with actuators and/or couplings associated with one or more components of the access sheath 90, the scope 40, and/or the basketing device 30. For example, as the scope 40 is retracted once the object 80 has been captured by the basket 35, force readings on one or more components of the instruments may be analyzed to determine whether such forces exceed predetermined thresholds indicative of a stuck-instrument condition. In some implementations, the sensitivity of such stuck-instrument determinations can be improved by implementing basket dithering in accordance with embodiments of the present disclosure.

Basket dithering may be implemented when the scope 40 and/or basket 35 enter a hazard zone 99, wherein the hazard zone 99 may be an area in which the risk of instrument sticking/catching is relatively high. For example, the stuck-instrument hazard zone 99 may generally cover an area at or near the ureteropelvic junction 78 and/or the area immediately before (i.e., distal to) the opening of the access sheath 90, which may generally be associated with higher risks of catching on the urinary tract anatomy and the opening of the access sheath 90, respectively. For example, the narrowing of the urinary tract as the anatomy moves from the renal pelvis 71 into the ureter 63 presents a narrowing of the channel/cavity that can result in instrument catching where the basket 35 and/or stone/object 80 captured therein have a width/diameter or other dimension that is greater than certain dimensions of the anatomical passage. Furthermore, the opening of the access sheath 90 is generally narrower than the anatomy through which the basket 35 is retracted leading to the access sheath 90. Therefore, the access sheath 90 represents a relatively narrow passage, wherein the basket 35 and/or stone/object 80 captured therein can get stuck when the dimensions thereof are greater than a diameter of the access sheath opening. Therefore, the hazard zone 99 advantageously includes one or both of the narrowing area of the ureteropelvic junction 78 and the area immediately in front of the opening 93 of the access sheath 90. In some embodiments, the area of the hazard zone 99 may be determined based at least in part on the position of the opening/distal end of the access sheath 90, such that the hazard zone 99 occupies an area a predetermined distance in front of the access sheath 90.

Basket dithering may be implemented in order to amplify the differences in force signal between stuck-instrument conditions and non-stuck conditions. For example, slightly advancing and retracting the basket while the scope and basket or retracted can help ensure that stuck-instrument sensor readings are clearly identifiable. For example, the use of basket dithering, as described in detail herein, can result in reduced noise and/or improved sensitivity of force readings on the various instruments. For example, by implementing basket dithering, wherein the basket 35 is advanced and retracted some distance in an oscillating manner, the effects of static friction forces can be reduced or obviated. Generally, static frictional forces may present when the basket 35 is in a relatively stationary position and in contact with the walls of the anatomy. With the basket 35 moving in an oscillating manner, the friction experienced on the instruments may be primarily of the form of kinetic friction, which is typically associated with a smaller coefficient of friction compared to static friction. Therefore, with basket dithering employed, the signal-to-noise ratio of the forces exerted on the various instrument components may be relatively higher compared to solutions in which the scope 40 and/or basket 35 or retracted without basket dithering.

As the basket is retracted into and through the hazard zone 99, force feedback readings on actuator(s) associated with one or more components of the basketing system 30, scope 40, and/or sheath 90 can be analyzed to determine when such forces increase in a manner consistent with stuck-instrument conditions and/or risk associated therewith. When such determinations are made, such as when force readings rise above a given threshold level, the retraction speed of the scope 40 and/or basket 30 can be automatically reduced, to thereby guide the user/operator to continue operation and/or retraction of the scope with increased caution.

In some embodiments, the basket 35 includes one or more electromagnetic sensors, wherein such sensors may provide sensor signals and/or otherwise indicate the position of the basket 35, wherein such positional information may serve as a basis to determine when the basket 35 is at or near the hazard zone 99. Furthermore, positional information determined using electromagnetic sensor(s) associated with the basket 35 can be used to trigger dithering initiation for stuck-instrument detection.

In order to provide for effective detection of stuck-instrument conditions and reduce the incidences of false positives with respect to stuck-instrument detection that can cause annoyance or distraction for the user, the stuck-instrument hazard zone 99 can be configurable to cover an area that is determined to be particularly prone to stuck-instrument risks. For example, the hazard zone 99 may be configurable based on a position of the access sheath 90, wherein the hazard zone 99 covers a certain distance before and/or around the distal opening of the access sheath 90. The dithering action of the basket 30c around the access sheath 90 can advantageously improve sensitivity of detection of a stuck basket 35c at the entrance/opening of the access sheath 90, whereas the dithering of the basket 35b farther away from the access sheath 90 can improve sensitivity of detection of stuck-basket conditions at or near the relatively narrow opening of the ureteropelvic junction 78.

In some cases, the precise position of the scope 40 and/or access sheath 90 is/are unknown. For example, estimation of the scope and/or sheath position may be based on one or more of robotic arm/mechanism position(s); knowledge/data indicating scope length, sheath length, and/or other known data; Scope is longer/farther than thought, feed roller arm that holds the UAS, could add uncertainty; determined position data based on data generated using one or more positional sensors; camera image analysis, and/or the like. However, such measurements may not be associated with sufficiently tight tolerances in some cases. Generally, it may be desirable to take into account the entire relevant tolerance chain in order to ensure that the stuck instrument determination features disclosed herein are implemented in a zone/area that includes the distal end of the access sheath 90 to ensure that such features are implemented until the basket is safely within the access sheath.

In some implementations, image processing may be implemented to identify that the scope 40 is within the access sheath 90 prior to discontinuing certain stuck instrument detection mechanism(s). For example, discontinuation of one or more of the stuck instrument determination mechanisms disclosed herein may be triggered at least in part by a visual identification (e.g., either by physician/technician analysis or digital image processing) of one or more features associated with the inside and/or distal end of the access sheath.

In situations in which access sheath position tolerances lead to a range of area in which the distal end of the access sheath may be, it may be desirable to operate according to a relatively expansive hazard zone to ensure that the access sheath is positioned at least partially therein. Therefore, although the illustrated hazard zone 99 is shown as ending at or near the actual position of the opening 93 of the access sheath 90, it should be understood that in some implementations, the zone in which certain of the disclosed stuck instrument determination mechanisms disclosed herein are executed may extend farther into the ureter 63 than is shown in FIG. 5, and or to cover an area overlapping the distal end of the access sheath 90. In some embodiments, the hazard area 99 in which certain stuck instrument determination mechanism(s) are executed includes an area corresponding to the range of the scope 40. That is, the hazard zone 99 may extend as far into the kidney 70 as the scope 40 and/or basket 30 can and/or does reach.

As described in detail herein, the force reading(s) that may be utilized as inputs for determining stuck instrument conditions can include force readings indicating forces present on one or more of the scope drive (i.e., insertion and/or retraction) actuator(s)/pulley(s), access sheath coupling(s), basket sheath insertion/retraction actuator(s), basket tine insertion/retraction actuator(s), and/or torque sensors on one or more robotic arms or other robotic components (e.g., insertion/retraction rail-type systems). For example, with reference back to FIGS. 4A-4E, forces on the distal drive feed rollers/pulleys 38 can be resolved to determine stuck instrument conditions. Although force sensors are described throughout the present disclosure, it should be understood that such sensors may be any types of sensors configured to generate and/or provide signal(s) indicating forces experienced on an actuator, coupling, and/or other mechanical component of a mechanical and/or robotic system/device, including direct torque sensors, electrical current sensors, and/or the like.

In connection with any of the disclosed embodiments, stuck instrument conditions can be determined based on sensor readings indicating forces on any type of insertion and/or retraction mechanism(s), whether such mechanism(s) drive insertion and/or retraction of an access sheath, endoscope, basketing sheath, basketing tines, or other component of a surgical system. For example, sensor data upon which stuck instrument condition determination may be based can be generated and/or provided by sensor(s) associated with a rail-based instrument driving system. Such sensor data may advantageously indicate tug force on one or more components of the system. In some embodiments, such insertion/retraction mechanics can be implemented as a virtual or actual rail system, wherein such system is configured to produce linear (i.e., rail-type) motion of one or more components of a surgical system. The insertion/retraction forces detected using such sensors can serve as a basis for stuck instrument condition determination.

Vision-Based Stuck-Instrument Determination

In some implementations, endoscope camera images can provide a basis for stuck-instrument determination. Such vision-based stuck-instrument determination functionality may be implemented by control circuitry of a medical system using certain image-processing techniques. FIG. 6A shows a field-of-view 701 of an endoscope camera with a basketing device 35 viewable therein in accordance with one or more embodiments of the present disclosure. FIG. 6B shows a side view of a medical instrument assembly corresponding to the configuration of the basketing device 35 relative to the endoscope camera 48 used to capture the image 701 of FIG. 6A in accordance with one or more embodiments. In the image 701, the basket 35 and stone 80 are relatively large in the field-of-view due to the proximity of the basket 35 to the scope camera 48.

FIG. 7A shows a field-of-view 702 of the endoscope camera 48 with the basketing device 35 in a stuck condition viewable therein in accordance with one or more embodiments of the present disclosure. FIG. 7B shows a side view of the medical instrument assembly of FIG. 6B corresponding to the configuration of the basketing device 35 relative to the endoscope camera 48 shown in FIG. 7A in accordance with one or more embodiments. Compared to the images of the basket 35 and stone 80 in the image 701 of FIG. 6A, the images of the basket 35 and stone 80 in the image 702 of FIG. 7A are smaller in size and positioned higher in the image frame 702. Such changes in image size and/or position can be caused by, and provide an indication of, the basket 35 having become stuck as the scope 40 is retracted. Therefore, image processing mechanisms configured to identify material changes in image size and/or position with respect to basket tines and/or captured object(s) can be implemented to determine a stuck-instrument condition.

Unlike solutions in which basketing system actuator forces exclusively are used to detect/determine stuck-instrument conditions, some embodiments of the present disclosure involve implementing vision analysis/processing to determine stuck-instrument conditions. For example, images captured by the endoscope camera can provide information relating to stuck-instrument conditions. For example, in the scope images may be processed to determine and/or estimate a distance between the distal end/tip of the scope 40, which may generally be associated with the camera 48 of the scope and thus the camera view window 701, 702 presented to the user, and the basket 35, or portion thereof, or stone 80.

The endoscope image 701 associated with FIG. 6A may be representative of an image captured by the endoscope 40, wherein the basket 35 is not stuck, and therefore is viewable as relatively close to the camera 48 of the endoscope 40 in the field of view 701. As shown in FIG. 6B, which may generally be considered to correspond to the image 701 captured by the scope camera 48 shown in FIG. 6A, the stone 80 may be a distance $d_1$ that is relatively close to the distal end of the scope 40.

The image 702 of FIG. 7A shows the stone 80 at a greater distance $d_2$ from the end of the scope 40. Such greater distance $d_2$ may be a result of the basket 35 and/or stone 80 having become stuck on certain anatomy or instrumentation, and therefore retraction of the scope 40 causes the basketing device 30 to pull out of the working channel 44 of the scope 40. Therefore, in the image 702, the stone 80 and basket 35 are shown in a relatively smaller size, indicative of the position of the stone 80 and basket 35 farther away from the scope camera 48 due to the increase in distance of the stone 80 and basket 35 away from the scope camera 48.

In some implementations, control circuitry of a medical device or system may be configured to determine shapes and/or sizes associated with stone and/or basket features visible in a camera view, wherein such shape and/or distance information may be used to determine a change in distance of a stone and/or basket, and/or an absolute distance determination thereof with respect to the camera of the endoscope. Therefore, a determination that a basket and/or stone is smaller in a subsequent image compared to a previously-captured image may indicate that a stuck-instrument condition is present. Certain remedial action may be implemented in response to such determinations, as described in detail herein.

In some embodiments, electromagnetic sensors, or other positional sensors, associated with the basket 35 and/or basketing device 30 may be used to determine a position of the basket 35 relative to the position of the scope 40, which may be indicated by positional sensor(s) associated with the distal end of the scope 40. Such positional information may be used to determine a distance between the basket 35 and the scope 40, wherein such distance may indicate stuck-instrument conditions.

In some embodiments, basket tines may have color-type characteristics that are at least partially stress-dependent. For example, such tines may be configured such that, in the presence of a stress loads caused by a stuck-basket condition, a change is manifest in the visual characteristics of the basket, as viewable in the field-of-view of the camera of the endoscope. That is, the displayed camera image presented to the user may have colored characteristics that indicate to the user the stresses experienced by the basket, and therefore indicate stuck-instrument conditions. In some embodiments, optical fibers may be utilized to provide shape-sensing functionality. For example, a basket may be fitted with relatively thin optical fibers that have a grading that can be interrogated by stimulating with, for example, a pulse train of light, wherein control circuitry of the system is configured to interpret such readings and make stuck-instrument determinations based at least partially thereon.

Figure 8:
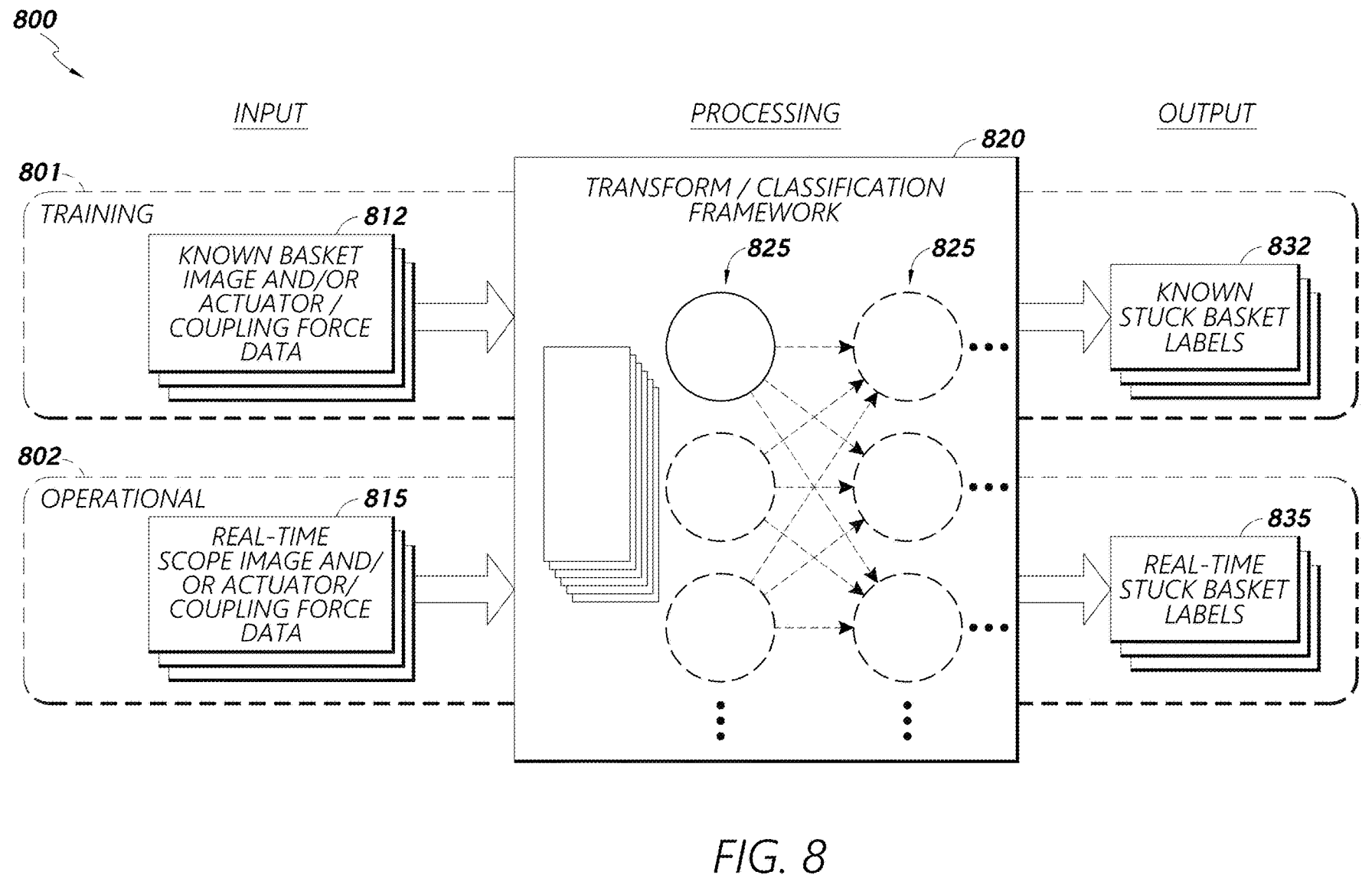

FIG. 8 illustrates a stuck-instrument architecture 800 in accordance with one or more embodiments. The architecture 800 provides a framework (e.g., a feature-identification and/or force-sensor-analysis framework) for identifying one or more instrument, anatomical, and/or stone/object features in endoscope camera images and/or one or more robotic actuator/coupling forces associated with one or more components of a robotic surgical system for dynamically determining/identifying stuck-instrument conditions based on characteristics thereof in accordance with one or more embodiments of the present disclosure. The framework 800 may be embodied in certain control circuitry, including one or more processors, data storage devices, connectivity features, substrates, passive and/or active hardware circuit devices, chips/dies, and/or the like. For example, the framework 800 may be embodied at least in part in the control circuitry 251 and/or control circuitry 211 shown in FIG. 2 and described above. The framework 800 may employ machine learning functionality to perform automatic stuck-instrument condition determination/detection on, for example, ureteroscopic images of internal renal anatomy, wherein the images include certain instrument components and/or kidney stones or other objects. Additionally or alternatively, the framework 800 may employ machine learning functionality to perform automatic stuck-instrument condition determination/detection on, for example, robotic endoscope and/or basketing actuator forces, as described in detail herein.

The framework 800 may be configured to operate on certain image-type data structures, such as image data representing at least a portion of a treatment site associated with one or more medical procedures and/or instrument components used in such procedure(s). In some embodiments, the framework 800 may be configured to operate on robotic actuator force profile data, as described herein. Such input data/data structures may be operated on in some manner by certain transform circuitry 820 associated with an image-processing portion of the framework 800. The transform circuitry 820 may comprise any suitable or desirable transform and/or classification architecture, such as any suitable or desirable artificial neural network architecture.

The transform circuitry 820 may be trained according to known images and/or actuator/coupling force profiles 812. For example, image data may contain representations of medical instrument components (e.g., baskets) and/or kidney stones or other objects and target labels 832 corresponding to the respective images 812 as input/output pairs, wherein the transform/classification framework 820 is configured to adjust one or more parameters or weights associated therewith to correlate the known input and output image data. Additionally or alternatively, the data 812 may comprise robotic actuator/coupling force reading profiles that may be provided as input to the transform/classification framework 820 and the transform/classification framework 820, wherein the transform circuitry is configured to correlate the known force profiles with known stuck instrument output labels. For example, the transform circuitry 820 (e.g., convolutional neural network) may be trained using a labelled dataset and/or machine learning. In some implementations, the machine learning framework may be configured to execute the learning/training in any suitable or desirable manner.

The known target labels 832 may be generated at least in part by manually labeling images and/or force profiles as being associated with stuck instrument conditions or not. For example, manual labels may be determined and/or applied by a relevant medical expert to label where, for example, basket components/structures are in the images and/or whether representations of basket components/structures and/or force profiles indicate a stuck-instrument condition. The known input/output pairs can indicate the parameters of the transform circuitry 820, which may be dynamically updatable in some embodiments.

The known stuck-instrument labels 832 may identify the boundary and/or the internal area of the target instrument features present therein and/or may indicate whether the relevant images correspond to a stuck-instrument condition. In some embodiments, the framework 800 may be configured to generate the real-time target labels 835 in a manner as to indicate in a binary manner whether a particular image and/or force profile of the real-time data 815 indicates a stuck-instrument condition or not.

The framework 800 may further be configured to generate the real-time target label 835 associated with real-time scope images 815 using the trained version of the transform circuitry 820. For example, during retraction of a medical instrument (e.g., basket and/or scope) during a medical procedure, real-time scope images showing the medical instrument may be processed using the transform circuitry 820 to generate the real-time target labels 835 identifying the presence of a stuck-instrument condition in the real-time images. For example, in some implementations, ureteroscope images may be processed by the transform circuitry 820 to identify a stuck basket. User notification of the same may be provided in response to the real-time stuck-instrument label determination 835.

The transform framework 820 may comprise an artificial neural network, such as a convolutional neural network. For example, the framework 820 may implement a deep learning architecture that takes in an input image, assigns learnable weights/biases to various aspects/objects in the image to differentiate one from the other. Filters/characteristics of the framework 820 may be hand-engineered or may be learned through machine learning.

The framework 820 may include a plurality of neurons 825 (e.g., layers of neurons, as shown in FIG. 8) corresponding to overlapping regions of an input image that cover the visual area of the input image. The framework 820 may further operate to flatten the input image, or portion(s) thereof, in some manner. The framework 820 may be configured to capture spatial and/or temporal dependencies in the input images 815 through the application of certain filters. Such filters may be executed in various convolution operations to achieve the desired output data. Such convolution operations may be used to extract features, such as edges, contours, and the like. The framework 820 may include any number of convolutional layers, wherein more layers may provide for identification of higher-level features. The framework 820 may further include one or more pooling layers, which may be configured to reduce the spatial size of convolved features, which may be useful for extracting features which are rotational and/or positional invariant, as with certain anatomical features. Once prepared through flattening, pooling, and/or other processes, the image data may be processed by a multi-level perceptron and/or a feed-forward neural network. Furthermore, back-propagation may be applied to each iteration of training. The framework may able to distinguish between dominating and certain low-level features in the input images and classify them using any suitable or desirable technique. In some embodiments, the neural network architecture comprises any of the following known convolutional neural network architectures: LeNet, AlexNet, VGGNet, GoogLeNet, ResNet, or ZFNet.

The framework 800 may be trained with a sufficient amount of driving data, such as endoscope image data, wherein a truth table may be generated based on known labels of stuck-instrument conditions and non-stuck-instrument conditions. During operation, the real-time images 815 and/or other driving information may be used as inputs to the system 820 to provide the real-time stuck-instrument predictions/results as output 835.

Stuck-Stone Condition Management Processes

Figures 1, 9, 10:
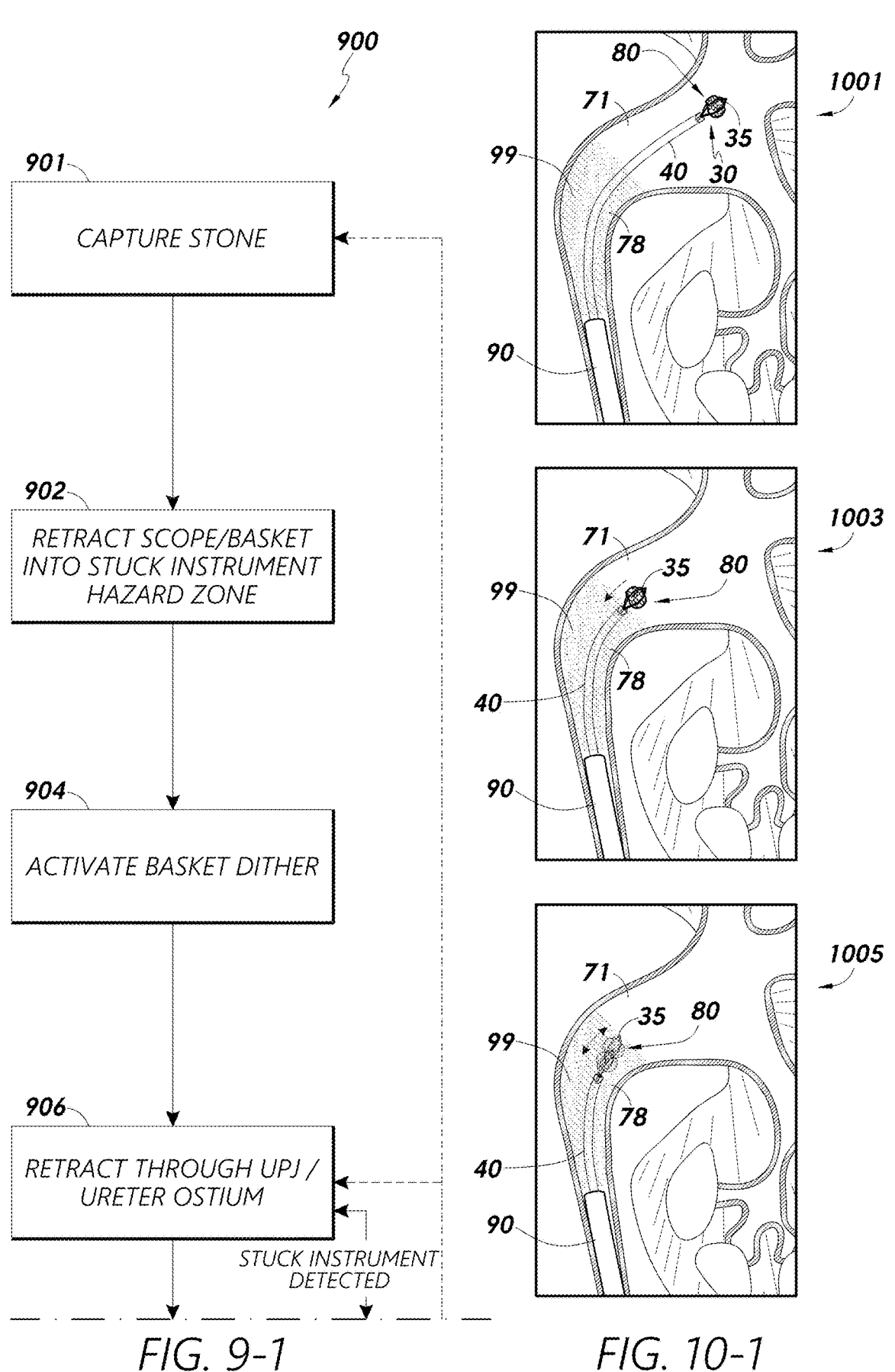

FIGS. 9-1 and 9-2 show a flow diagram illustrating a process 900 for managing stuck-instrument conditions in accordance with one or more embodiments. FIGS. 10-1 and 10-2 shows certain images corresponding to various blocks, states, and/or operations associated with the process 900 of FIGS. 9-1 and 9-2 in accordance with one or more embodiments. In executing the process 900 of FIG. 9, a user may provide certain controls through a control system coupled to a robotic basketing system (e.g., a robotic system having one or more instrument device manipulators (IDM) coupled thereto for controlling a basketing device and/or scope). Such control system may provide real-time endoscope camera images, and/or other information relating to the procedure. In some embodiments, one or more aspects of the process 900 may be implemented by control circuitry of a control system coupled to the robotic basketing system and/or control circuitry associated with the robotic basketing system. Various force sensor readings relating to the various operational steps of the process 900 can be provided by the robotic system, which may be configured to determine torque/force readings on one or more actuators of the robotic basketing system.

At block 901, the process 900 involves capturing a stone with a basket 35 within an anatomical cavity of the patient. For example, the stone 80 may be captured in the area of the renal anatomy beyond the ureteropelvic junction 78, as shown in the image 1001 of FIG. 10-1. At block 902, the process 900 involves retracting the scope 40 and/or basket 35 into a stuck-instrument hazard zone 99, as shown in image 1003 of FIG. 10-1.

The determination that the basket 35 has entered the stuck-instrument hazard zone 99 can be based at least in part on one or more basket-localization mechanisms that can be used to localize the position of the basket 35 within the anatomy and/or certain phases of the procedure. The hazard zone 99 may include, for example, the ureteropelvic junction 78 and/or the area immediately distal/in-front-of the opening 93 of the access sheath 90. Determination that the basket 35 is in the hazard zone 99 may be achieved in any suitable or desirable way. In some embodiments, the position of the basket 35 may be indicated by commands of the robotic system controlling the scope 40 and/or basket 35. For example, additional known information relating to the position of the scope 40 relative to the distal end 93 of the sheath 90 may provide information indicating the position of the basket 35 and/or distal end of the scope 40. The position of the basket 35 may be determined using any suitable or desirable localization mechanism. In some embodiments, basket dithering and/or basket localization may be triggered upon entry of the basket 35 and/or scope 40 into the ureteropelvic junction 78 and/or hazard zone 99. In some implementations, localization of the basket 35 and/or basket dithering may be automatically triggered in response to the determination of successful capture of the stone 80.

At block 904, the process 900 involves activating dithering of the basket 35, as shown in image 1005 in FIG. 10-1. Such dithering action may advantageously improve the sensitivity of the relevant force sensor readings associated with one or more actuators/couplings of the robotic mechanisms used to control the scope 40 and/or basket device 30. Dithering may be implemented in accordance with any of the embodiments disclosed herein. For example, dithering may involve a relatively slow motion of advancement and retraction of the basket 35 relative to the scope 40. The dithering distance may advantageously be relatively short to reduce the effects of dithering on the user control/experience. The dithering speed implemented may be set to a speed that is slower than the normal driving speed of the scope 40. Furthermore, the dithering distance may be set to be a fraction of the overall basket travel range/distance in order to avoid disturbing or confusing the operating physician/technician during basket retraction.

Although the flow diagram of FIG. 9 describes retracting the basket 35 into the hazard zone 99, in some implementations, basket dithering and/or other stuck-instrument detection functionality may be automatically triggered when the stone 80 is captured by the basket 35 and/or such functionality may be ceased when the basket 35 has safely entered into the access sheath 90. In some implementations, stuck-basket determination based on force readings from sensor(s) associated with robotic control actuator(s) or coupling(s) may be implemented without implementing basket dithering. That is, any of the embodiments disclosed herein for stuck-instrument determination may be performed/implemented with or without basket dithering.

In some implementations, certain preventative measures/functionality may be implemented to prevent stuck-instrument conditions. For example, some embodiments provide a mechanism wherein the robotic system is configured to cause the basket to slip/advance forward in a manner that mimics or is similar to manual basketing adjustment when stuck-instrument forces are detected. In this way, the stuck instrument force that can result in physiological and/or instrumentation damage can be set greater than such slip force, wherein after a stuck-instrument condition has been detected, the user can manually resolve the stuck-instrument condition and place the basket back into the non-slip position.

At block 906, the process 900 involves retracting the basket 35 and/or distal end of the scope 40 through the ureteropelvic junction/ureter transitional area/ostium. For example, retraction in connection with the operations of block 906 can be performed while the basket 35 is dithering, as shown in image 1005, which may provide desired sensor sensitivity for stuck instrument deduction. If forces detected at one or more actuators associated with the basketing device 30 and/or endoscope 40 indicate a stuck-instrument condition, the process 900 may proceed to block 910, wherein certain stuck-instrument remedial action may be implemented.

Stuck-instrument detection may be based one or more torque/force readings on one or more axes/actuators associated with the robotic basketing system, such as torque/force experienced at a basket-insertion driver/actuator (e.g., engaged with the basketing sheath). In some implementations, a determination that a stuck-instrument condition is present may be based on a determination that the basket insertion axis force experienced at one or more actuators associated with the basket sheath and/or basket tines is greater than a predetermined threshold for a threshold amount of time. For example, in some embodiments, when a first force and/or time threshold is met, remedial action involves slowing down the scope retraction speed to allow for sufficient time for stuck-instrument detection functionality to be implemented and/or to reduce force generated by the stuck basket to reduce the magnitude and/or risk of harm caused thereby. In some embodiments, after the retraction speed has been slowed-down, if basket forces continue to increase beyond another predetermined threshold level, such as a fault threshold level, retraction of the scope may be halted to prevent damage and allow for correction of the stuck-instrument condition.

In embodiments in which the remedial action associated with block 910 involves halting/stopping retraction of the scope in response to the determined stuck-instrument condition, such operation may serve to prevent or reduce the risk of user error, such as may occur when the physician/technician is not paying adequate attention to the endoscope images and/or tactile feel of the instrumentation when retracting the scope 40 and/or basket 30.

When no stuck-instrument condition is determined, the process 900 proceeds to block 908, where the basket 35 and/or distal end of the scope 40 is/are retracted into the access sheath 90 through the distal opening 93 thereof. If a stuck-instrument condition is detected in connection with retraction into the sheath 90, the process 900 may proceed to block 910, where remedial action associated with the stuck-instrument condition may be implemented in any suitable or desirable way.

The remedial action associated with block 910 can allow the user to clear the stuck-instrument fault, readjust the basket/stone position, and continue retraction in some cases that allow for recovery. After remedial action a block 910, the process 900 may continue back to any of the subsequent steps of the process and/or may result in a termination of the process at block 916. After successful remedial action in connection with block 910, further force readings beyond relevant threshold levels can result in re-triggering of and/or returned to remedial action at block 910.

At block 912, the process 900 involves deactivating basket dithering. For example, such deactivation of dithering may be triggered by determination that the basket 35 and/or distal end of the scope 40 has entered the access sheath 90. At block 914, the process 900 involves retracting the basket through the access sheath 90. Such retraction through the access sheath 90 may be done at an accelerated speed in some implementations. That is, once within the access sheath 90, retraction speeds may be increased to reduce procedure times and/or for other purposes relating to convenience and/or efficiency. Once the basket has been retracted through the access sheath 90, the process 900 may be terminated at block 916.

Figure 11:
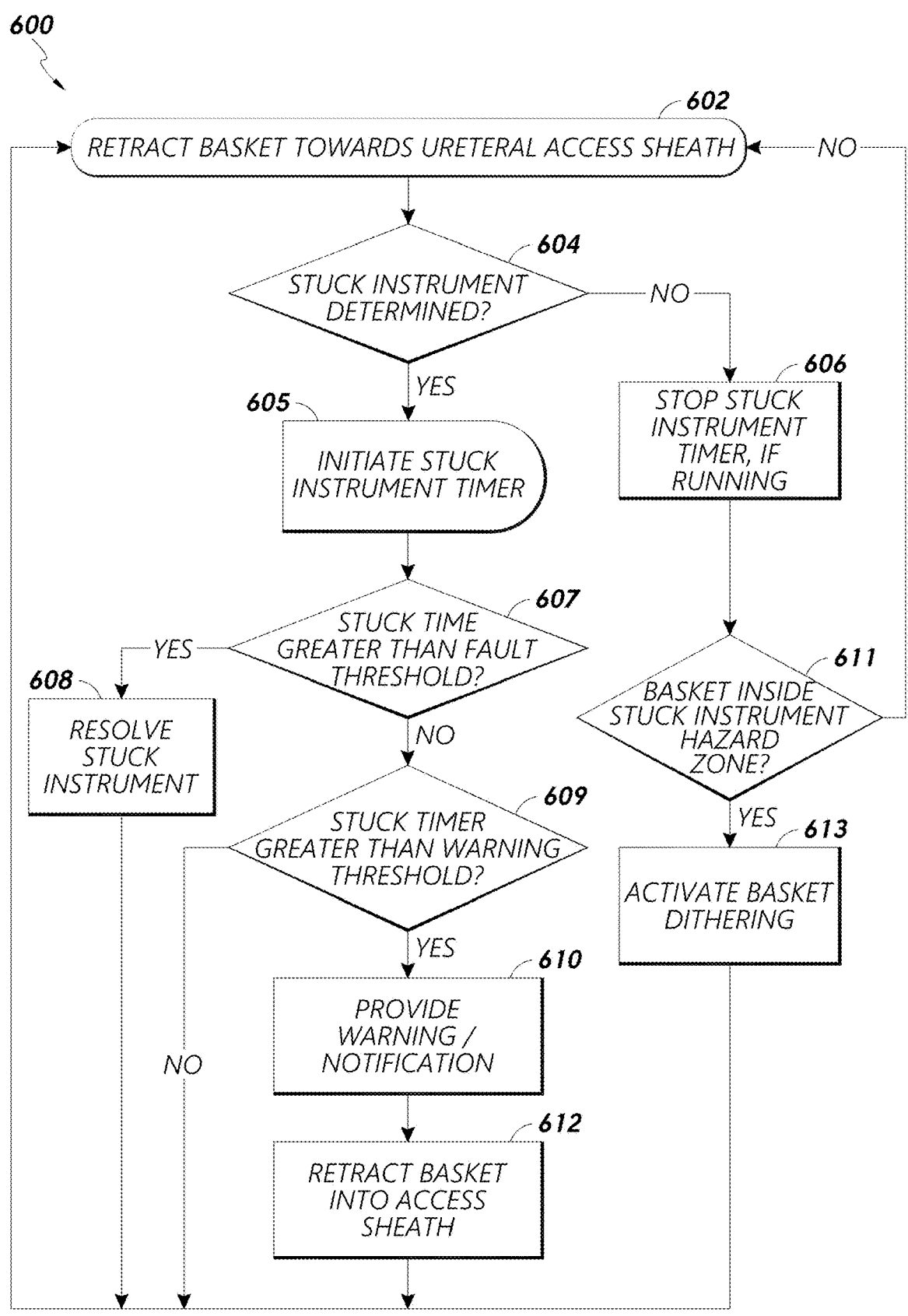
FIG. 11 is a flow diagram illustrating a process for handling stuck-instrument conditions in accordance with one or more embodiments.

FIG. 11 is a flow diagram illustrating a process 600 for handling stuck-instrument conditions in accordance with one or more embodiments. At block 602, the process 600 involves retracting a basket having an object (e.g., stone) captured therein towards a ureteral access sheath. For example, the basket may be retracted with an endoscope, wherein the basket is posed within a working channel of the endoscope.

At block 604, the process 600 involves determining, based on force readings from sensor(s) associated with robotic scope- and/or basketing-control actuator(s), whether the basket is in a stuck-instrument condition. For example, the determination at the decision block 604 may involve determining that a force reading at one or more actuators of the basketing system is greater than a predetermined stuck-instrument detection threshold. In some implementations, the determination at block 604 may be executed while the basket is operating in a dithering motion, which may provide relatively greater sensitivity for stuck-instrument detection/determination, as described in detail herein.

The determination of whether forces experienced at one or more actuator(s) of the basketing and/or robotic system indicates a stuck-instrument condition may be supplemented and/or informed by certain other information/data relating to the procedure and/or user. For example, information relating to the particular anatomy of the patient, the operator's driving behavior, and/or stone size information may be used as inputs to determine whether the present conditions indicate a stuck-instrument condition in connection with decision block 604. In some implementations, control circuitry configured to determine stuck-instrument conditions may be adaptive at least in part and configured to predict likely stuck-instrument conditions and adjust input parameters associated with such determinations to further improve stuck-instrument detection accuracy.

If the force reading(s) analyzed in connection with block 604 indicate a stuck-instrument condition, a timer may be initiated at block 605. The timer may run for a period of time that the force reading(s) exceed the relevant threshold. That is, the period of time associated with block 605 may correspond to a period of time during which force reading(s) associated with one or more actuators of a robotic basketing system remain above a stuck instrument threshold level.

If the time that the force(s) exerted on the relevant actuator(s) remain above the predetermined threshold is greater than a fault threshold, as determined at decision block 607, the process 600 may proceed to block 608. For example, if the amount of time, as indicated by the stuck-instrument timer, that the forces on the basket and/or scope exceed the stuck-instrument threshold is greater than the fault threshold, a minor fault may be thrown, wherein the operator is not permitted to further retract the basket/scope until the stuck-instrument condition is resolved at block 608.

If the period of time that the forces on the actuator(s) are greater than the stuck instrument threshold is not long enough to trigger the fault condition associated with block 608, but is greater than a predetermined warning threshold, the process 600 proceeds to block 610, where a warning or other notification may be generated and/or provided to a user indicating the stuck-instrument condition and/or risk thereof. Such warning may prompt the operator/user to adjust the basket and/or proceed with retraction of the basket with caution.

In addition to providing a user warning, in some implementations, the process 600 involves reducing a retraction speed of the scope and/or basketing device in response to one or more of the determination that the stuck-instrument condition is present at block 604, the determination that the timer period is greater than the warning threshold at block 609, and/or the determination that the timer period is greater than the fault threshold at block 607. Reducing the speed of retraction can help prevent forces from spiking without enough time to stop retraction and prevent physiological and/or instrument damage. In some embodiments, the stuck-instrument timer may be reset every time the detected forces drop below the predefined stuck-instrument force threshold to reduce the risk that noisy data will be filtered and a single spike on the basket forces triggers a false alarm. At block 612, the process 600 involves retracting the basket and scope into the access sheath.

If stuck-instrument conditions are met at either of box 607 or 609, or where no stuck-instrument condition is determined at block 604, the process 600 may proceed to block 606, where the stuck-instrument timer, if running presently, is stopped. At decision block 611, the process 600 involves determining whether the basket and/or distal end of the endoscope is within a stuck-instrument hazard zone. If so, the process 600 involves activating basket dithering in accordance with aspects of the present disclosure at block 613. If the basket and/or distal end of the endoscope are not yet within the stuck instrument hazard zone, the process 600 may return to block 602, where retraction of the basket/scope towards the ureteral access sheath continues.

False Positive Handling

Figure 12:
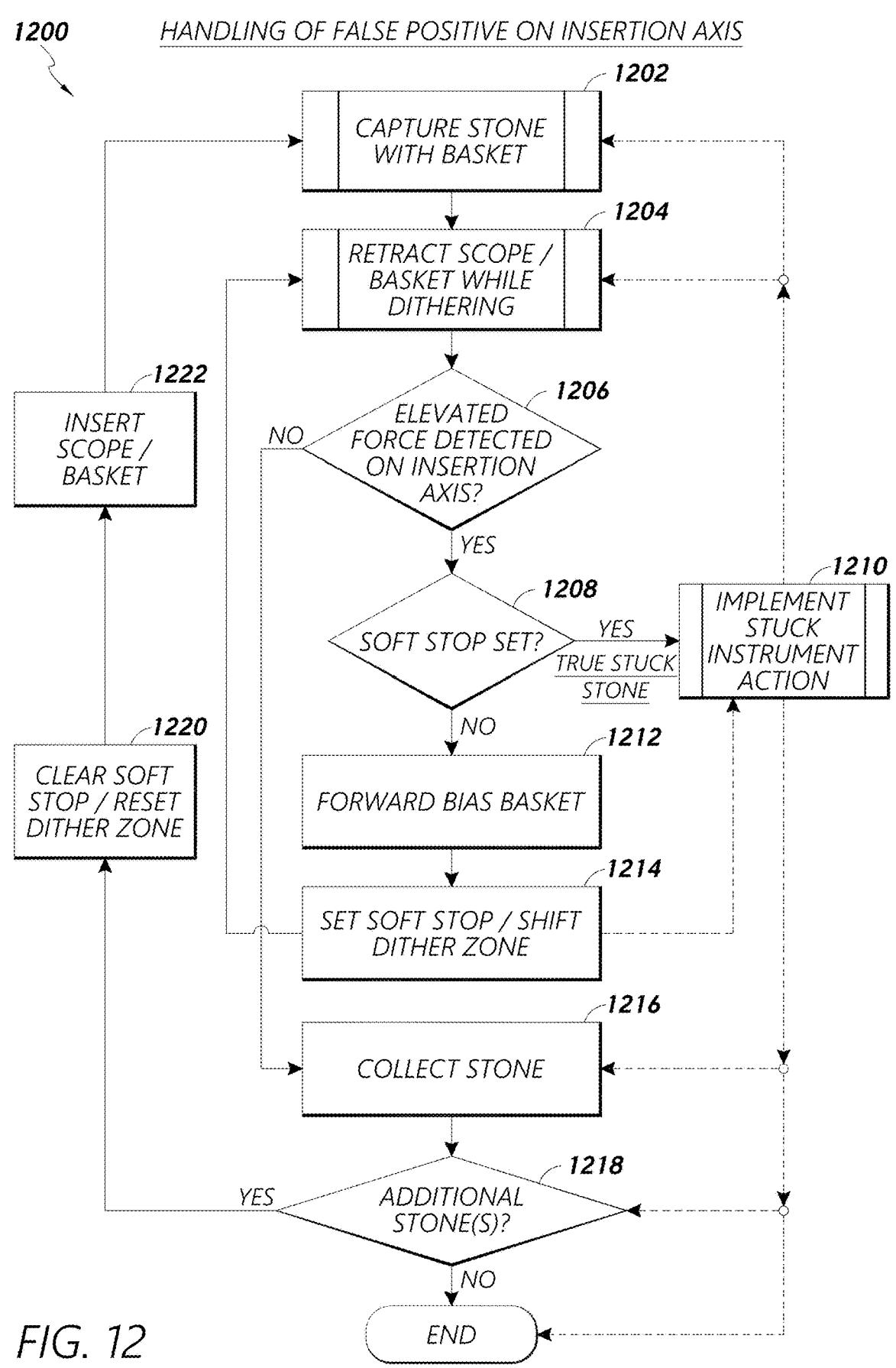
FIG. 12 is a flow diagram illustrating a process for managing false positive sensor readings on an insertion axis in accordance with one or more embodiments.

FIG. 12 is a flow diagram illustrating a process 1200 for managing false positive sensor readings on a basketing device insertion axis in accordance with one or more embodiments. At block 1202, the process 1200 involves capturing a stone with a basketing device within a kidney of a patient. For example, a stone fragment of a plurality of stone fragments may be captured. The stone may be captured by actuating an open axis of the basketing device, which may control the opening and closing of the basket tines/wires by extending the tines/wires from and/or retracting into a sheath of the basketing device. Capturing the stone may further involve actuating the insertion axis of the basketing device, which may cause actuation of the basket sheath so as to cause insertion and/or retraction of the basket relative to the endoscope in which the basketing device is disposed (e.g., within a working channel of the scope).

At subprocess block 1204, the process 1200 involves retracting the scope and basket while dithering the basket relative to the distal end of the scope, as described in detail herein. Such dithering may be implemented within a stuck instrument hazard zone, wherein the dithering process is implemented for stuck stone detection as described in detail throughout the present disclosure. During scope retraction, which may involve proximally retracting the scope and basket inside the access sheath used to access the target anatomy (e.g., ureteral access sheath) and/or a certain distance distal/outside of the distal end/opening of the access sheath, the basket insertion axis may be dithered forward and back to provide improved sensitivity for stuck instrument detection, as described in detail above. Generally, the dithering distance/range of motion may be set to a relatively small distance, such that it may not be noticeable by the user, while still generating dynamic movement for the basket insertion axis to provide improved stuck instrument detection sensitivity.

At block 1206, it is determined whether an elevated force is detected on the insertion axis associated with the basketing device. For example, one or more force sensors associated with the sheath of the basketing device may indicate elevated force that may potentially be indicative of a stuck stone condition. The insertion axis may be associated with a slider/actuator of a handle/cartridge associated with the basketing device, wherein the slider actuator is configurable to control insertion and retraction of the basket and/or sheath thereof relative to the scope when the basket is disposed within the working channel of the scope.

As described in detail above, robotic manipulator (e.g., robotic instrument device manipulator (IDM), end effector, etc.) torque sensing may be used as a source of input for stuck instrument detection. For example, stuck instrument detection functionality in accordance with aspects of the present disclosure may be implemented to detect insertion axis force peaks/levels that may occur when a true stuck instrument condition is present, such that the user may be notified of the potential stuck instrument condition before damage or injury to instrumentation and/or anatomy occurs. The elevated force detection associated with block 1206 may relate to the force on the insertion axis rising high enough to reach a threshold level, at which point scope slowdown may be implemented as a stuck instrument remedial action in some cases; scope retraction speed may be reduced to avoid insertion axis forces rising too fast to allow the system to throw a fault triggering stuck instrument remedial action. If no elevated force is detected on the insertion axis at block 1206, the process 1200 proceeds to block 1216, where the captured stone is collected, such as proximal to the access sheath used for accessing the target anatomy.

If an elevated force is detected on the insertion axis at block 1206, the process 1200 proceeds to decision block 1208, where it is determined whether a soft stop position (e.g., soft stop position providing a buffer distance from a possible hard stop position) has previously been set with respect to the insertion axis (e.g., a soft stop position relating to movement of the insertion axis slider/actuator). For example, a soft stop position may serve as a software limit on the motion (e.g., proximal and/or retraction motion) of the basket slider/actuator configured to control the insertion axis (e.g., basket sheath insertion/retraction). Therefore, where a soft stop position has been set, dithering and/or other motion (e.g., retraction) of the insertion axis of the basketing device may be limited artificially at a position that is not a physical hard stop position. In some implementations, detection of elevated force on the insertion axis triggers recordation/setting of a hard stop insertion axis actuator position for future reference as a position associated with a potential physical hard stop.

If a soft stop position has previously been set, the process 1200 proceeds to block 1210, where stuck instrument remedial action is implemented. That is, where elevated force is detected on the insertion axis after a soft stop position has previously been set, it may be determined that the elevated force on the insertion axis is indicative of a true stuck instrument condition, and therefore remedial action is warranted. Stuck instrument remedial action may involve slowing scope retraction to avoid insertion axis forces rising too fast to allow the system to throw a fault. If the insertion axis force continues to rise while slow scope retraction is implemented, a stuck instrument warning/fault may be thrown to notify the user of the potential stuck instrument condition and to trigger cessation/halting of scope retraction. Stuck instrument remedial action may involve soliciting an acknowledgement of the stuck instrument condition and/or resolution thereof from the user/practitioner.

If no soft stop position has previously been set/recorded, certain operations may be implemented to determine whether the elevated force detected on the insertion axis at block 1206 represents a false positive condition that is not in actuality a result of a stuck instrument condition, but rather possibly caused by contact with a physical hard stop by the insertion axis actuator. For example, the slider/actuator may hit the physical limit (e.g., back/proximal limit) of the track in which it slides/actuates. The basketing device/system may include a proximal basketing cartridge/handle including one or more actuators, such as an insertion axis actuator and/or an open axis actuator (controls the movement of the basket tines within the basket sheath, described in greater detail below with respect to FIGS. 19 and 20). When the basketing cartridge/handle is coupled or engaged with the robotic manipulator (e.g., end effector), the positions of the actuators may be unknown or may be at arbitrary or offset positions, such that they may or may not be within close range of a hard stop position in their respective tracks during various stages of the process 1200. Therefore, when an elevated insertion axis force is sensed and a soft stop position has not previously been set, the process 1200 proceeds to block 1212, where the insertion axis and/or basket may be forward biased relative to the scope by some predetermined distance/amount. That is, the basket may be advanced forward by some amount (e.g., nominal amount) to offset the basket and associated actuator from the position at which the elevated insertion axis force was detected. Forward biasing of the insertion axis, in the case that the elevated force was caused by contact with a hard stop on the insertion axis, can move the insertion axis actuator farther away from the true hard stop boundary, with the basket protruding relatively farther from the distal end of the scope as a result.

In addition to advancing/biasing forward the basket relative to the distal end of the scope, the process May 1200 involve, at block 1214, setting a soft stop position associated with the position of the insertion axis/basket at the time when the elevated force on the insertion axis was detected. For example, the soft stop position may be at the determined/suspected hard stop position, or the recorded soft stop position may advantageously be positioned a buffer distance (i.e., soft stop buffer) away from the determined/suspected hard stop position. That is, the soft stop position that is set/recorded may be a position that is distal (i.e., further inserted) with respect to the position of the basket at the time/point where the elevated force was detected. The soft stop position may thereby be set at a position that provides a buffer between the soft stop position and the potential hard stop position where the elevated force was detected. Setting the soft stop may prevent the insertion axis actuator from moving to the position at which the elevated insertion axis force was detected, which may be associated with a physical hard stop of the insertion axis actuator/slider.

In addition to setting the soft stop position and/or as a result of setting the soft stop position, the process 1200 may further involve, as a means of determining whether the elevated force on the insertion axis was from a hard stop of the insertion axis actuator/slider and therefore potentially a false positive reading not indicating a true stuck instrument condition, shifting the dithering range of motion forward for implementation when dithering the basket to an area that is distal to the soft stop position. The modified dithering zone may be limited on one end (e.g., proximal end) by the recorded soft stop position and/or the identified hard stop position.

After forward biasing of the basket, setting the soft stop position, and/or shifting forward the dithering zone, the process 1200 may return to subprocess 1204, where the basket and scope are retracted while implementing basket dithering, or the process 1200 may proceed to stuck instrument remedial operation(s) at block 1210. Although the flow diagram of FIG. 12 describes the subprocess 1204 as involving dithering of the basket, it should be understood that the process 1200 may be implemented without implementing basket dithering and/or shifting the dithering zone. The process 1200 can continue from the subprocess 1204, wherein since the soft stop position has previously been set, if an elevated force is subsequently detected on the insertion axis at block 1206, the process 1200 will proceed to the remedial action operation(s) at block 1210, wherein such elevated force may be interpreted as an indication of a true stuck instrument condition. If no further elevated force is detected after forward biasing the insertion axis/basket, it may be determined that the previously detected elevated force was associated with a true hard stop condition with respect to the insertion axis actuator. In some implementations, a hard stop position with respect to the insertion axis may be recorded/maintained in some manner for at least the duration of the coupling of the basketing cartridge/handle with the robotic manipulator (e.g., end effector) until disengagement thereof.

After collecting the captured stone at block 1216, it may be determined, at block 1218, whether additional stones and/or stone fragments remain to be collected. If so, the process may proceed to block 1220, where any previously-set soft stop position may be cleared/reset, and/or the dithering zone may be returned/reset to the default range/zone. The scope and basket are inserted back into the target anatomy at block 1222, after which an additional stone/fragment is captured at block 1202.

Figure 13:
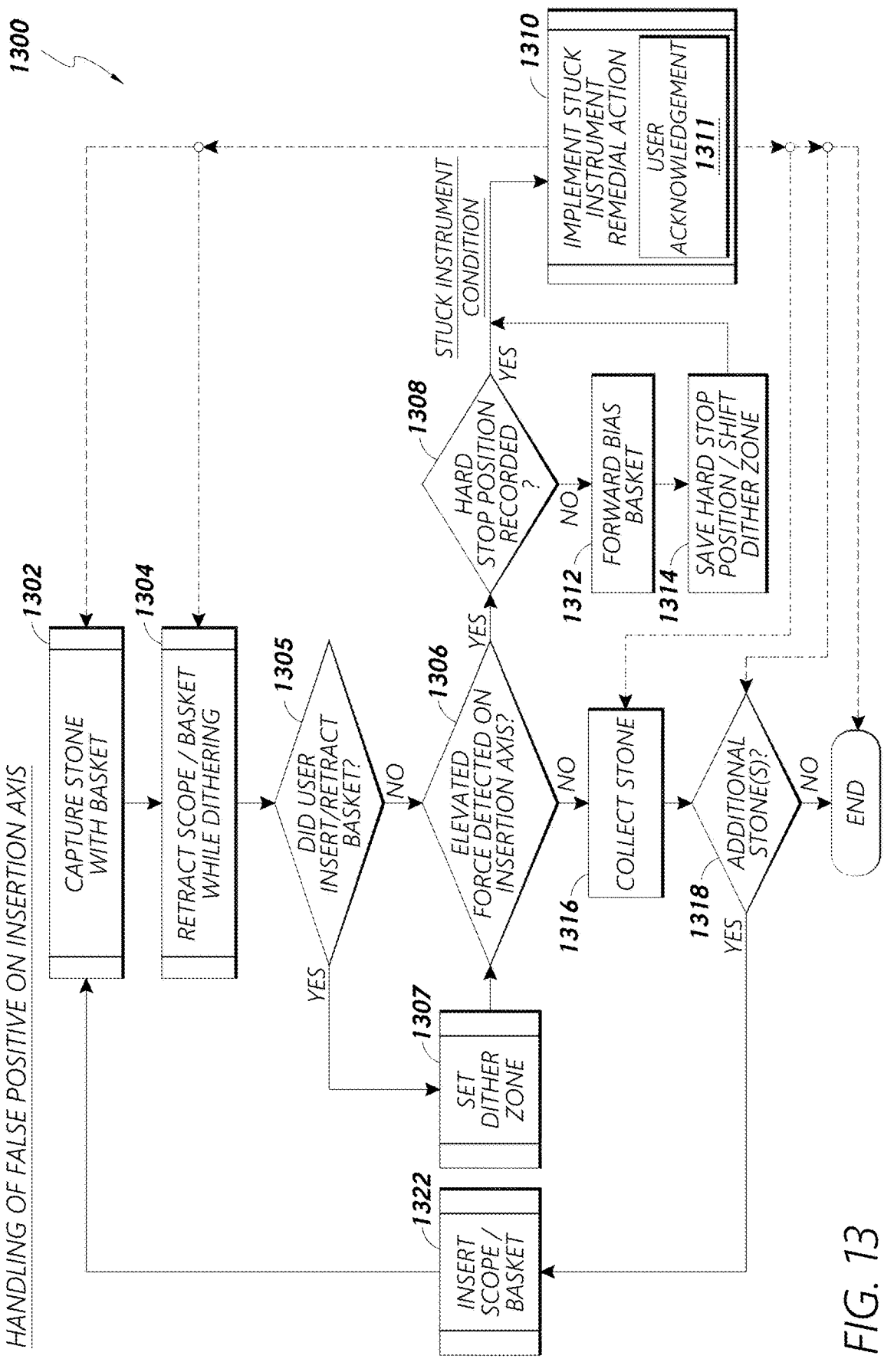
FIG. 13 is a flow diagram illustrating a process for managing false positive sensor readings on an insertion axis in accordance with one or more embodiments.

FIG. 13 is a flow diagram illustrating a process 1300 for managing false positive sensor readings on a basketing device insertion axis in accordance with one or more embodiments. At block 1302, the process 1300 involves capturing a stone with a basketing device within a kidney of a patient. For example, a stone fragment of a plurality of stone fragments may be captured. The stone may be captured by actuating an open axis of the basketing device, which may control the opening and closing of the basket tines/wires by extending the tines/wires from and/or retracting into a sheath of the basketing device. Capturing the stone may further involve actuating the insertion axis of the basketing device, which may cause actuation of the basket sheath so as to cause insertion and/or retraction of the basket relative to the endoscope in which the basketing device is disposed (e.g., within a working channel of the scope).

With further reference to FIG. 13, the blocks 1305 and 1307 of the process 1300 can be implemented to reset the dither zone of the basketing device with respect to dithering actuation of the insertion axis of the basketing device in the event that the user has moved the basket outside of (or within) the originally-set dither zone. At decision block 1305, it is determine whether the user has inserted or retracted the basket from a default position. For example, the determination at block 1305 can involve determining whether the user has actuated the insertion axis of the basketing device, such as by manually or robotically manipulating the insertion axis actuator/slider. For example, when the scope is being retracted, the basket may generally dither within a predetermined dither zone/range. If the user inserts or retracts the basket for some reason independently of the dithering motion of the basket, and subsequently continues scope retraction, then it may be desirable to modify the range of the dither zone.

If the basket has been inserted or retracted by the user, the process 1300 may proceed to block 1307, where the dithering zone for the basket may be modified/set to compensate for the insertion or retraction of the basket implemented by the user. For example, if the user has inserted the basket by some amount, the dithering zone may be moved forward by a commensurate amount; similar modification can be implemented for the retraction case.

At subprocess block 1304, the process 1300 involves retracting the scope and basket while dithering the basket relative to the distal end of the scope, as described in detail herein. Such dithering may be implemented within a stuck instrument hazard zone, wherein the dithering process is implemented for stuck stone detection as described in detail throughout the present disclosure. During scope retraction, which may involve proximally retracting the scope and basket together inside the access sheath used to access the target anatomy (e.g., ureteral access sheath) and/or a certain distance distal/outside of the distal end/opening of the access sheath, the basket insertion axis may be dithered forward and back to provide improved sensitivity for stuck instrument detection, as described in detail above. Generally, the dithering distance/range of motion may be set to a relatively small distance, such that it may not be noticeable by the user, while still generating dynamic movement for the basket insertion axis to provide improved stuck instrument detection sensitivity. Although the flow diagram of FIG. 13 describes the subprocess 1304 as involving dithering of the basket, it should be understood that the process 1300 may be implemented without implementing basket dithering and/or shifting the dithering zone.

At block 1306, it is determined whether an elevated force is detected on the insertion axis associated with the basketing device. For example, one or more force sensors associated with the sheath of the basketing device may indicate elevated force that may potentially be indicative of a stuck stone condition. The insertion axis may be associated with a slider/actuator of a handle/cartridge associated with the basketing device, wherein the slider actuator is configurable to control insertion and retraction of the basket and/or sheath thereof relative to the scope when the basket is disposed within the working channel of the scope.

As described in detail above, robotic manipulator (e.g., robotic instrument device manipulator (IDM), end effector, etc.) torque sensing may be used as a source of input for stuck instrument detection. For example, stuck instrument detection functionality in accordance with aspects of the present disclosure may be implemented to detect insertion axis force peaks/levels that may occur when a true stuck instrument condition is present, such that the user may be notified of the potential stuck instrument condition before damage or injury to instrumentation and/or anatomy occurs. The elevated force detection associated with block 1306 may relate to the force on the insertion axis rising high enough to reach a threshold level, at which point scope slowdown may be implemented as a stuck instrument remedial action in some cases; scope retraction speed may be reduced to avoid insertion axis forces rising too fast to allow the system to throw a fault triggering stuck instrument remedial action. If no elevated force is detected on the insertion axis at block 1306, the process 1300 proceeds to block 1316, where the captured stone is collected, such as proximal to the access sheath used for accessing the target anatomy.

If an elevated force is detected on the insertion axis at block 1306, the process 1300 proceeds to decision block 1308, where it is determined whether a hard stop position has previously been set/recorded with respect to the insertion axis (e.g., a hard stop position relating to movement of the insertion axis slider/actuator). The referenced hard stop position may be an actual confirmed physical hard stop limit, or another positional limit that is identified as a potential hard stop limit.

If a hard stop position has previously been set, the process 1300 proceeds to block 1310, where stuck instrument remedial action is implemented. That is, where elevated force is detected on the insertion axis after a hard stop position has previously been recorded, it may be determined that the elevated force on the insertion axis is indicative of a true stuck instrument condition, and therefore remedial action is warranted. Stuck instrument remedial action may involve slowing scope retraction to avoid insertion axis forces rising too fast to allow the system to throw a fault. If the insertion axis force continues to rise while slow scope retraction is implemented, a stuck instrument warning/fault may be thrown to notify the user of the potential stuck instrument condition and to trigger cessation/halting of scope retraction. Stuck instrument remedial action may involve soliciting an acknowledgement of the stuck instrument condition and/or resolution thereof from the user/practitioner.

If no hard stop limit/position has previously been set/recorded, certain operations may be implemented to account for the possibility that the elevated force detected on the insertion axis at block 1306 represents a false positive condition that is not in actuality a result of a stuck instrument condition, but rather possibly caused by contact with a physical hard stop by the insertion axis actuator. For example, the slider/actuator may hit the physical limit (e.g., back/proximal limit) of the track in which it slides/actuates. The basketing device/system may include a proximal basketing cartridge/handle including one or more actuators, such as an insertion axis actuator and/or an open axis actuator (for control of movement of the basket tines within the basket sheath; described in greater detail below with respect to FIGS. 19 and 20). When the basketing cartridge/handle is coupled or engaged with a robotic manipulator (e.g., end effector), the positions of the actuators may be unknown or may be at arbitrary or offset positions, such that they may or may not be within close range of a hard stop position in their respective tracks during various stages of the process 1300. Therefore, when an elevated insertion axis force is sensed and a potential hard stop limit position has not previously been set, the process 1300 proceeds to block 1312, where the insertion axis and/or basket may be forward biased relative to the scope by some predetermined distance/amount. That is, the basket may be advanced forward by some amount to offset the basket and associated actuator from the position at which the elevated insertion axis force was detected (i.e., the potential hard stop limit). Forward biasing of the insertion axis, in the case that the elevated force was caused by contact with a hard stop on the insertion axis, can move the insertion axis actuator farther away from the true hard stop boundary, with the basket protruding relatively farther from the distal end of the scope as a result. The forward biasing of the basket can give the basket a buffer (or greater buffer) from the proximal physical hard stop of the insertion axis.

In addition to advancing/biasing forward the basket relative to the distal end of the scope, the process May 1300 involve, at block 1314, recording a potential hard stop position associated with the position of the insertion axis/basket at the time when the elevated force on the insertion axis was detected. The process May 1300 further involve shifting the dithering zone/range of motion forward for implementation when dithering the basket to an area that is farther distal by some distance. Such distance may be a buffer distance away from the recorded hard stop position, such that the proximal limit of the dither zone/range is a soft stop position separated from the hard stop position by the buffer distance. After recording the potential hard stop position, if it is determined subsequently that the insertion axis can drive past such limit without a physical hard stop, then the recorded hard stop position can be modified accordingly.

After forward biasing of the basket, recording the hard stop position, and/or shifting forward the dithering zone, the process 1300 may proceed to the remedial operation(s) associated with block 1310, and ultimately further to allow for continued retraction of the scope in connection with block 1304. The process 1300 can continue from the subprocess 1304, wherein since the hard stop position has previously been recorded, if an elevated force is subsequently detected on the insertion axis at block 1306, the process 1300 will proceed to the remedial action operation(s) at block 1310, wherein such elevated force may be interpreted as an indication of a true stuck instrument condition. If no further elevated force is detected after forward biasing the insertion axis/basket, the process 1300 may proceed through to collection without incident. At block 1310, the system may throw a fault, after which the user may acknowledges the fault (block 1311) to verify whether there is a true stuck instrument condition. Once the fault is acknowledged, the user may be permitted to drive the scope again (e.g., return to block 1302 or 1304).

After collecting the captured stone at block 1316, it may be determined, at block 1318, whether additional stones and/or stone fragments remain to be collected. If so, the process may proceed to block 1322, where the scope and basket are inserted back into the target anatomy, after which an additional stone/fragment is captured at block 1302.

Figure 14:
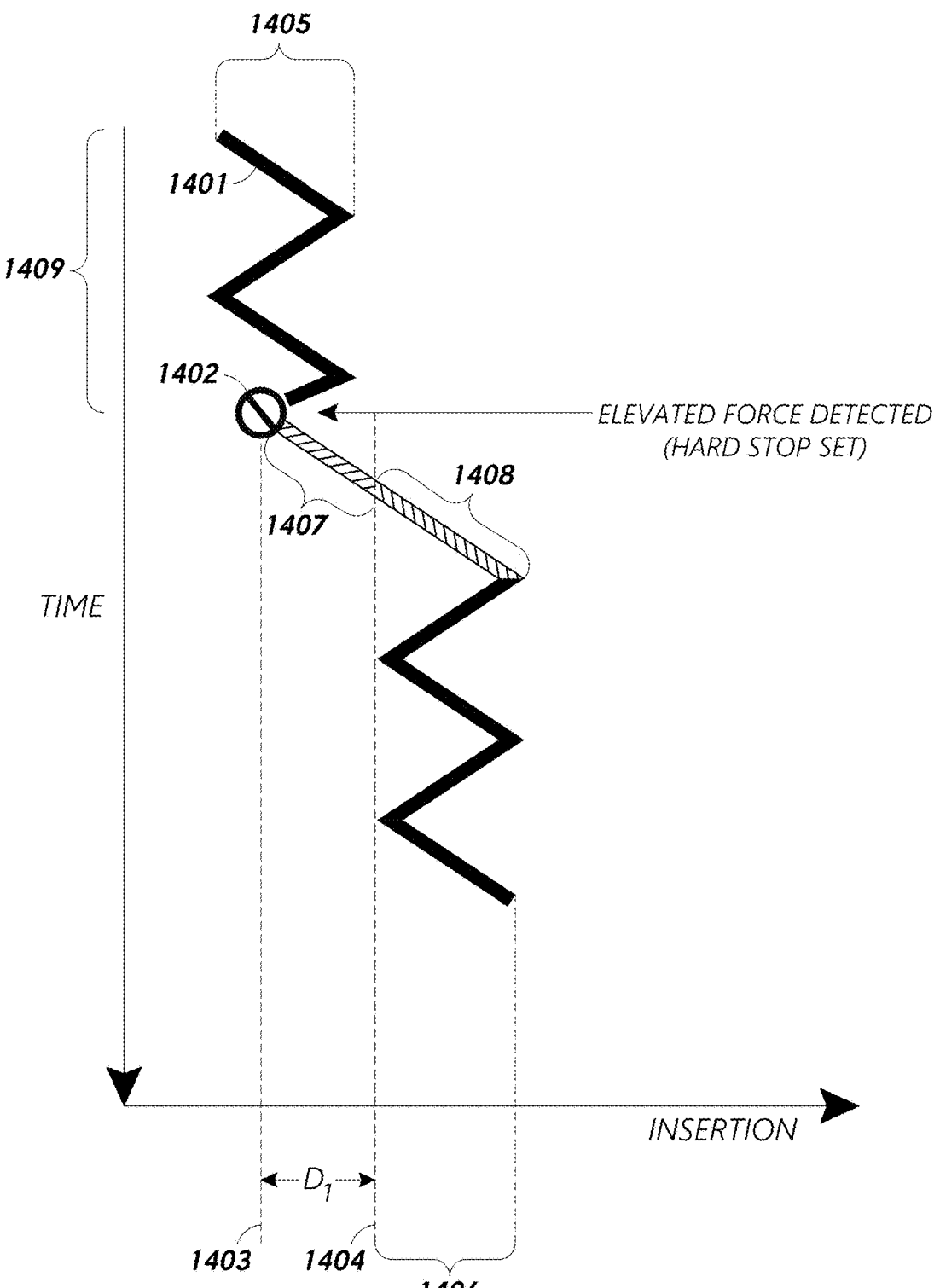
FIG. 14 is a diagram showing false positive remedial action in accordance with one or more embodiments.

FIG. 14 is a diagram showing hard stop force detection remedial action in accordance with one or more embodiments. The diagram of FIG. 14 includes a time axis moving from the top of the page to the bottom, with time advancing in such direction, and an insertion axis running, and increasing, from left to right and representing the relative distance of the basket with respect to the distal end of the scope. The zigzag movement of the line 1401 indicates the dithering motion of the basket relative to the scope by actuation of the insertion axis actuator/slider, as described in detail herein. The dithering action of the basket may be within a predetermined dithering zone/range of motion 1405 during a first window of time 1409.

At a point 1402 representing a particular point in time while dithering the basket and/or a corresponding basket insertion position 1403, an elevated force is detected on the insertion axis, which may be caused by a true stuck instrument condition, or may be a false positive reading caused by the insertion axis actuator/slider hitting a physical hard stop position. For example, the slider/actuator may hit the back/physical limit of the track in which it slides/actuates. In response, the position where the elevated force on the insertion axis was detected may be stored, set, and/or otherwise recorded as a hard stop position.

In response to the detected elevated force on the insertion axis, the basket may be forward biased by a distance, which may be equal to and/or related to the illustrated distance $D_1$, wherein such forward biasing of the basket is represented by the line segment 1407 and/or at least a portion of the line segment 1408. A soft stop insertion axis position 1404 may be set and/or enforced/implemented, wherein such soft stop basket insertion position 1404 may be the same as the hard stop position 1403, or may be forward biased by a distance $D_1$ relative to the hard stop position 1403, as shown. Furthermore, the dithering zone/range of motion for the dithering of the basket may be biased forward to a modified zone/range 1406, wherein the modified dithering zone/range 1406 may be determined and/or positioned such that the proximal most insertion position during the dithering action associated therewith does not cross the soft stop boundary 1404.

Figures 15, 16:
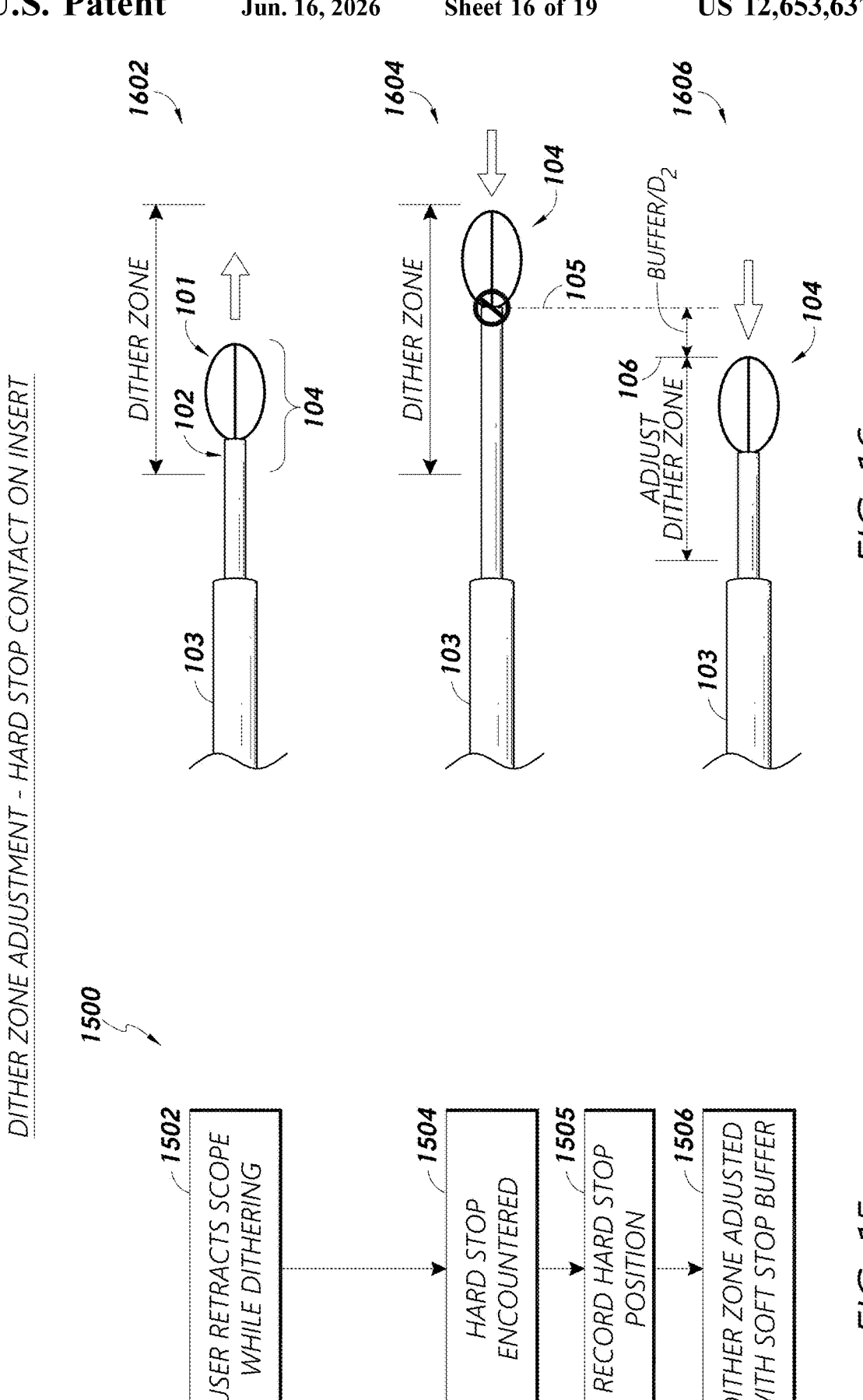
FIG. 15 shows a flow diagram illustrating a process for adjusting a dithering zone/range in accordance with one or more embodiments.
FIG. 16 shows certain images corresponding to various blocks, states, and/or operations associated with the process of FIG. 15 in accordance with one or more embodiments.

FIG. 15 shows a flow diagram illustrating a process 1500 for adjusting a dithering zone/range in accordance with one or more embodiments of the present disclosure, such as may be implemented in connection with the processes 1200 and 1300 described above. FIG. 16 shows certain images corresponding to various blocks, states, and/or operations associated with the process 1500 of FIG. 15 in accordance with one or more embodiments. In FIG. 16, the illustrated one-sided arrows may represent basket motion, such as motion relative to the scope 103.

The process 1500 provides for adjustment of the dither zone, such as in the event that the dithering motion of the basket during scope retract runs the basket insertion axis into a distal hard stop. For example, block 1502 involves the user retracting the scope while dithering the basket; the user may or may not be aware of the dithering of the basket as it may be implemented automatically as a responsive system process. The image 1602 shows the basket tines 101 and/or distal end of the basket sheath 102 dithering in the dither zone. The distal end 102 of the basket sheath and/or one or more portions of the basket 101 distal of the sheath 102 are referred to below as the basket 104; such references can refer to any of such components/portions.

At block 1504, the process 1500 involves detecting a hard stop when inserting the basket forward in connection with dithering motion. For example, it may be understood that elevated insertion axis force readings generated on basket insertion are likely or certainly a result of actuator hard stop contact; true stuck stone conditions may generally not produce a relatively high force during basket insertion. At block 1505, the process 1500 involves recording the insertion axis position 105 associated with the hard stop.

At block 1506, the process 1500 involves adjusting the dither zone proximally. In some implementations, such dither zone adjustment may include a buffer between the hard stop position 105 and the distal end 106 of the adjusted dither zone. For example, in connection with adjusting the dither zone, the insertion axis may be driven back by some distance to relieve the tension on the driver of the insertion axis actuator (e.g., robotic manipulator/end effector driver coupled in a driving engagement with the input of the basketing device cartridge/handle). The distance $D_2$ may be considered the soft stop buffer, which represents the distance the basket 104 is driven back to release the tension on the device and to prevent for continually bumping into the physical limits of the device/system.

Figures 17, 18:
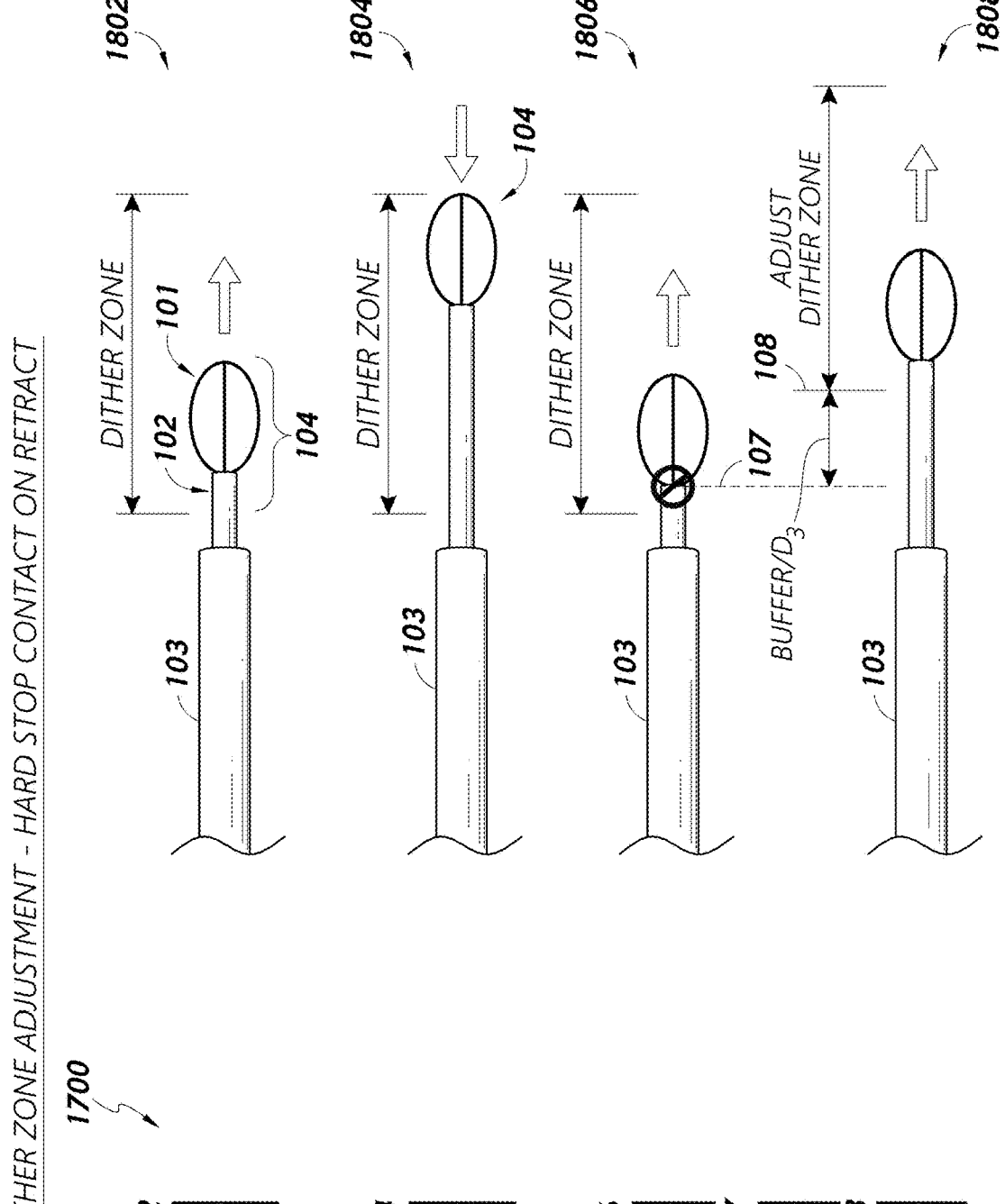
FIG. 17 shows a flow diagram illustrating a process for adjusting a dithering zone/range in accordance with one or more embodiments.
FIG. 18 shows certain images corresponding to various blocks, states, and/or operations associated with the process of FIG. 17 in accordance with one or more embodiments.

FIG. 17 shows a flow diagram illustrating a process 1700 for adjusting a dithering zone/range in accordance with one or more embodiments of the present disclosure, such as may be implemented in connection with the processes 1200 and 1300 described above. FIG. 18 shows certain images corresponding to various blocks, states, and/or operations associated with the process 1700 of FIG. 17 in accordance with one or more embodiments. In FIG. 18, the illustrated one-sided arrows may represent basket motion, such as motion relative to the scope 103.

The process 1700 provides for adjustment of the dither zone, such as in the event that the dithering motion of the basket during scope retract runs the basket insertion axis into a proximal hard stop. For example, block 1702 involves the user retracting the scope while dithering the basket; the user may or may not be aware of the dithering of the basket as it may be implemented automatically as a responsive system process. The image 1802 shows the basket tines 101 and/or distal end of the basket sheath 102 dithering in the dither zone. The distal end 102 of the basket sheath and/or one or more portions of the basket 101 distal of the sheath 102 are referred to below as the basket 104; such references can refer to any of such components/portions.

At block 1704, the process 1700 involves the dithering direction changing from forward insertion to backward retraction as a result of the basket 104 reaching the distal boundary of the dither zone. At block 1706, the process 1700 involves detecting a hard stop when retracting the basket backward in connection with dithering motion. At block 1705, the process 1700 involves recording the insertion axis position 107 associated with the hard stop.

At block 1706, the process 1700 involves adjusting the dither zone distally. In some implementations, such dither zone adjustment may include a buffer between the hard stop position 107 and the proximal end 108 of the adjusted dither zone. For example, in connection with adjusting the dither zone, the insertion axis may be driven forward by some distance to relieve the tension on the driver of the insertion axis actuator (e.g., robotic manipulator/end effector driver coupled in a driving engagement with the input of the basketing device cartridge/handle). The distance D₃ may be considered the soft stop buffer, which represents the distance the basket 104 is driven forward to release the tension on the device and to prevent for continually bumping into the physical limits of the device/system.

Figure 19:
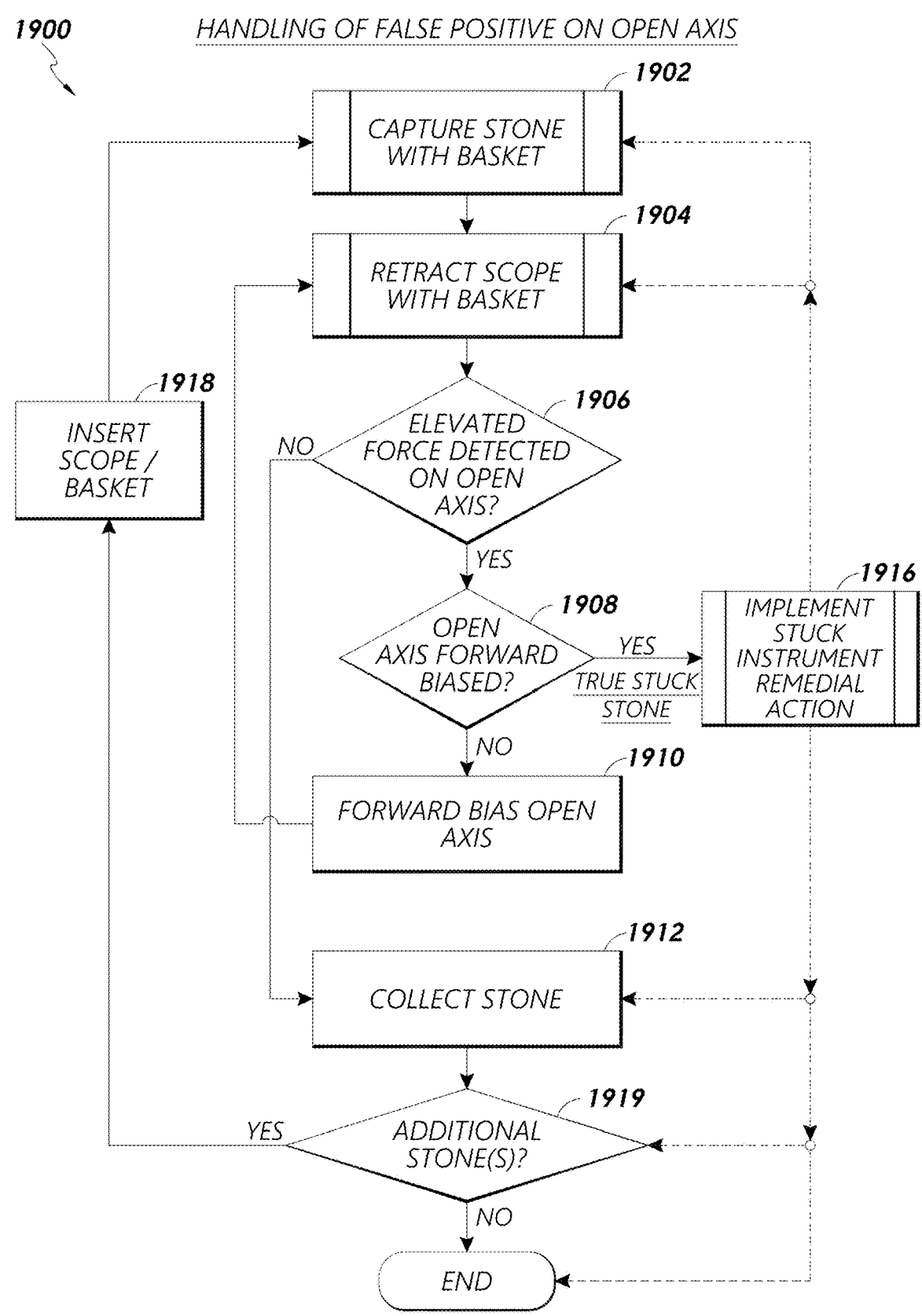
FIG. 19 is a flow diagram illustrating a process for managing false positive sensor readings on an open axis in accordance with one or more embodiments.

FIG. 19 is a flow diagram illustrating a process 1900 for managing false positive sensor readings on an open axis in accordance with one or more embodiments. As referenced above, stuck instrument conditions can result in relatively high forces being transferred to the basket open axis, and therefore it can be advantageous to monitor forces on the open axis in connection with stuck instrument management with respect to any of the embodiments of the present disclosure. For example, actuating a basket slider/actuator configured to actuate the basket tines relative to the basket sheath can be implemented for stone capture. As described above, such actuation may be considered "open axis" actuation, wherein forces and actuation relating thereto are on what may be considered the "open axis" of the basking system.

At block 1902, the process 1900 involves capturing a stone or stone fragment with a basking device deployed from a working channel of an endoscope (referred to herein as a "scope" for convenience). For example, capturing the stone with the basket may involve operating an open axis of the basketing device to draw one or more wire tines or other basket components into (or out of) a basking sheath and/or around the captured stone. The closing of the basket tines around the scope may be implemented at least in part by proximally (or in another manner) actuating the basket slider/actuator, wherein such actuator may be associated with a basketing cartridge associated with a proximal portion of the basking device/system and driven by a robotic manipulator. In some cases, when closing the basket tines around a stone/fragment, the tines become wedged against the sides of the basket sheath in a manner as to reduce the amount of force sensed on the open axis. However, in some instances, the tines may not close sufficiently tightly around the captured stone fragment, such that greater sensitivity to force readings on the open axis results; stuck instrument conditions can be felt on the open axis in some such instances.

A block 1904, the process 1900 involves retracting the scope and basket together proximally towards and/or into a distal opening of an access sheath through which the scope and basket access the target anatomical chamber/location. Decision block 1906 relates to whether an elevated force is detected on the open axis of the basking system during retraction in connection with block 1904. For example, the basketing device/system may include one or more force sensors associated with the open axis and configured to generate signals indicating forces experienced on the open axis, such as forces pulling on the basket tines.

If no elevated force is detected on the open axis, the process 1900 may proceed to complete retraction of the scope and basket and collect the stone/fragment in connection with the operation(s) associated with block 1912. If additional stones/fragments remain to be collected, as indicated at decision block 1919, the process may involve reinserting the scope and basket through the access sheath to the target anatomical chamber (e.g., calyx network of a kidney), as indicated at block 1918, and further loop back to the sub-process 1902 relating to the further capturing of one or more additional stones/fragments with the basket.

If an elevated force is detected on the open axis during scope and basket retraction as determined at block 1906, the process may continue to block 1908, where it may be determined whether the open axis is presently in a forward-biased position. For example, forward biasing of the open axis (e.g., basket tines) may have previously been implemented in connection with a previously detected elevated force on the open axis.

If the open axis was not previously forward biased, as determined at block 1908, the process 1900 may proceed with certain operations intended to identify and/or manage the possibility that the elevated force detected on the open axis was associated with a false positive condition not indicative of a true stuck instrument condition, such as may be the result of the open axis actuator/slider contacting a hard stop during retraction of the scope and basket. For example, such operations may involve forward biasing the open axis, such as by actuating in a forward/distal direction the open axis actuator/slider a predetermined distance, such as 1-5 mm, 5-10 mm, or more, as shown at block 1910. Forward biasing the open axis may be considered and/or implemented as setting a soft stop position associated with the forward-biased position of the open axis and driving to such position.

After forward-biasing the open access, the process 1900 may return to the retraction 1904 and/or stone-capture 1902 operations of the process 1900. If elevated force is detected on the open axis during stone capture and or scope/basket retraction after forward biasing of the open axis at block 1910, the path from decision block 1908 may proceed to block 1916 relating to stuck instrument remediation. For example, if elevated force is detected on the open axis after preventative forward biasing of the open axis actuator has been implemented, it may be determined that the elevated force is indicative of a true stuck instrument condition, and therefore the process 1900 may proceed to implement operations associated with remedial action for stuck instrument conditions, as described in detail herein area.

Figure 20:
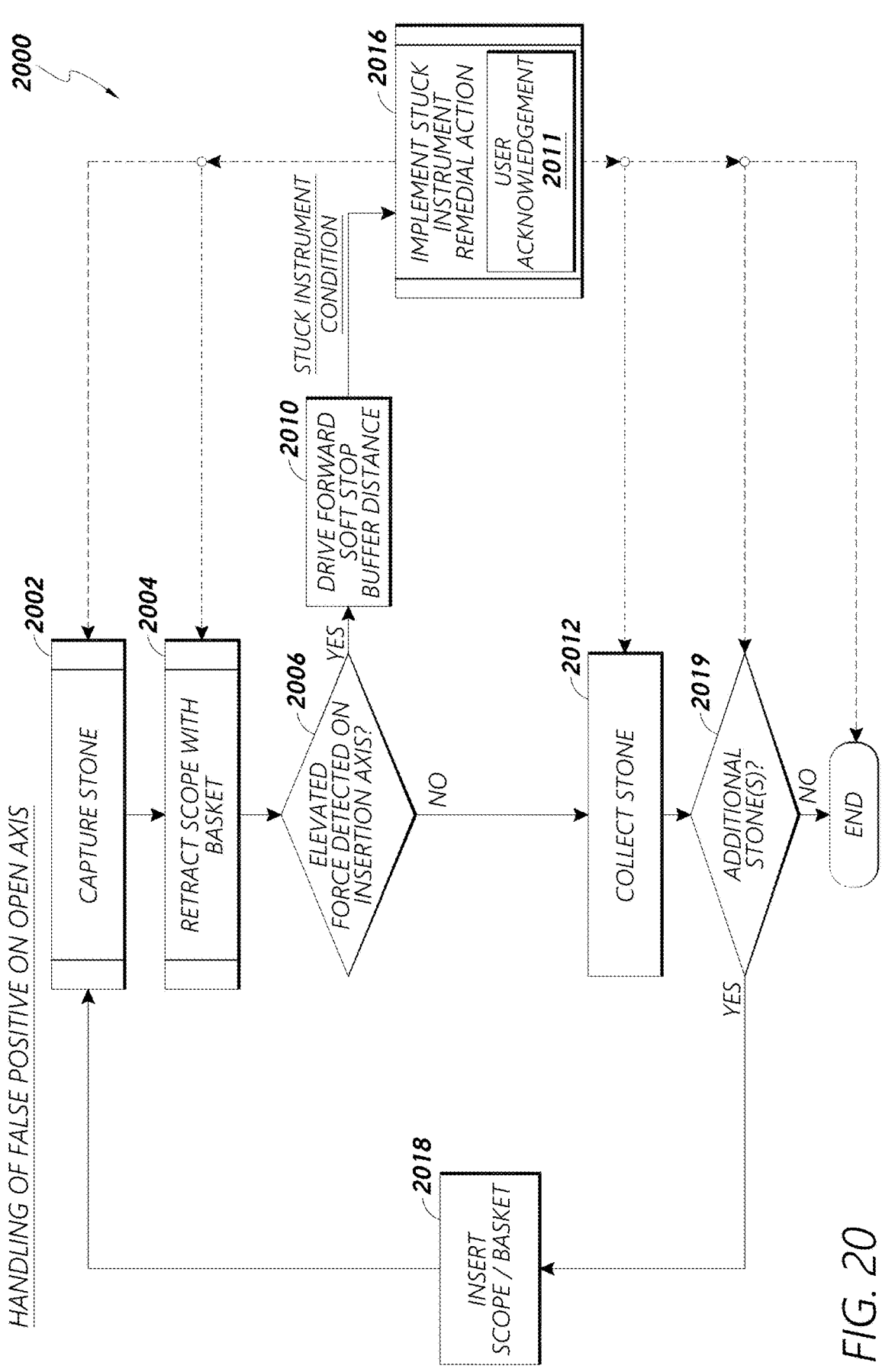
FIG. 20 is a flow diagram illustrating a process for managing false positive sensor readings on an open axis in accordance with one or more embodiments.

FIG. 20 is a flow diagram illustrating a process 2000 for managing false positive sensor readings on an open axis in accordance with one or more embodiments. As referenced above, stuck instrument conditions can result in relatively high forces being transferred to the basket open axis, and therefore it can be advantageous to monitor forces on the open axis in connection with stuck instrument management with respect to any of the embodiments of the present disclosure. For example, actuating a basket slider/actuator configured to actuate the basket tines relative to the basket sheath can be implemented for stone capture. As described above, such actuation may be considered "open axis" actuation, wherein forces and actuation relating thereto are on what may be considered the "open axis" of the basking system.

At block 2002, the process 2000 involves capturing a stone or stone fragment with a basking device deployed from a working channel of an endoscope (referred to herein as a "scope" for convenience). For example, capturing the stone with the basket may involve operating an open axis of the basketing device to draw one or more wire tines or other basket components into (or out of) a basking sheath and/or around the captured stone. The closing of the basket tines around the scope may be implemented at least in part by proximally (or in another manner) actuating the basket slider/actuator, wherein such actuator may be associated with a basketing cartridge associated with a proximal portion of the basking device/system and driven by a robotic manipulator. In some cases, when closing the basket tines around a stone/fragment, the tines become wedged against the sides of the basket sheath in a manner as to reduce the amount of force sensed on the open axis. However, in some instances, the tines may not close sufficiently tightly around the captured stone fragment, such that greater sensitivity to force readings on the open axis results; stuck instrument conditions can be felt on the open axis in some such instances.

A block 2004, the process 2000 involves retracting the scope and basket together proximally towards and/or into a distal opening of an access sheath through which the scope and basket access the target anatomical chamber/location. Decision block 2006 relates to whether an elevated force (e.g., force above a predetermined threshold) is detected on the open axis of the basking system during retraction in connection with block 2004. For example, the basketing device/system may include one or more force sensors associated with the open axis and configured to generate signals indicating forces experienced on the open axis, such as forces pulling on the basket tines.

If no elevated force is detected on the open axis, the process 2000 may proceed to complete retraction of the scope and basket and collect the stone/fragment in connection with the operation(s) associated with block 2012. If additional stones/fragments remain to be collected, as indicated at decision block 2019, the process 2000 may involve reinserting the scope and basket through the access sheath to the target anatomical chamber (e.g., calyx network of a kidney), as indicated at block 2018, and further loop back to the sub-process 2002 relating to the further capturing of one or more additional stones/fragments with the basket.

If an elevated force is detected on the open axis during scope and basket retraction as determined at block 2006, the process may continue to block 2010, which may involve driving the open axis forward a predetermined soft stop buffer distance, such as by actuating in a forward/distal direction the open axis actuator/slider a predetermined distance (e.g., 1-5 mm, 5-10 mm, or more). The forward driving/biasing of the open axis may be implemented to provide some clearance from the possible hard stop boundary/limit associated with the elevated force detected at block 2006.

Even though it may be unknown whether the elevated force is due to a stuck instrument condition or simply a hard stop collision/contact, the process 2000 may nevertheless proceed with similar stuck-instrument-related remedial actions as connected with block 2016. The forward-driving of the open axis may be considered part of the stuck instrument remedial actions associated with block 2016. Among possibly other things, the remedial actions associated with block 2016 can involve notifying the user of the potential stuck instrument condition. The user, in turn, may check camera view(s) and/or other parameter(s) to confirm whether a true stuck instrument condition is present. If so, the user may manipulate the basket, scope, and/or other instrument(s) to resolve the stuck instrument condition. Once the user acknowledges that the stuck instrument condition (block 2011), if any, has been resolved, the system may permit the further driving (e.g., retraction) of the scope. For example, the process 2000 may proceed to any of blocks 2002, 2004, 2012, 2019, or terminate in some manner.

In cases in which false positive handling as represented in FIGS. 12, 13, 19 and/or 20 is/are not implemented, elevated insertion and/or open axis forces triggered due to physical hard stop conditions with respect to respective actuator(s)/slider(s) and result in repeated faults being thrown due to the erroneous assumption that such elevated forces are due to stuck instrument conditions. Therefore, the processes illustrated in FIGS. 12-20 can enable stuck instrument management in accordance with embodiments of the present disclosure without the risk of fatal or problematic hard stop interference/derailment.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to".

What is claimed is:

1. A robotic system comprising:
one or more robotic manipulators;
one or more actuators associated with at least one of the one or more robotic manipulators and configured to cause axial movement of at least one of an endoscope, a sheath of a basket device disposed at least partially within the endoscope, or tines of the basket device;
one or more sensors associated with the one or more robotic manipulators and configured to generate signals indicating a force experienced by the one or more actuators; and
control circuitry communicatively coupled to the one or more robotic manipulators and the one or more sensors and configured to:
cause the basket device to advance and retract in a dithering motion;
while the basket device is moving in the dithering motion, receive the signals from the one or more sensors indicating the force experienced by the one or more actuators;
determine that the force is greater than a predetermined threshold; and
execute a responsive action in response to the determination that the force is greater than the predetermined threshold.

2. The robotic system of claim 1, wherein the responsive action involves providing a warning to a user indicating that the basket device is in a stuck state.

3. The robotic system of claim 1, wherein the responsive action involves reducing a retraction speed of the endoscope.

4. The robotic system of claim 1, wherein the responsive action involves halting retraction of the endoscope.

5. The robotic system of claim 1, wherein the one or more actuators comprise one or more basket sheath actuators.

6. The robotic system of claim 1, wherein the one or more actuators comprise one or more basket tine actuators.

7. The robotic system of claim 1, wherein the one or more actuators comprise one or more endoscope actuators.

8. The robotic system of claim 1, wherein the control circuitry is further configured to:
detect a hard stop force reading associated with at least one of an open axis or an insertion axis associated with the basket device; and
drive the at least one of the open axis or the insertion axis forward a using at least one of the one or more actuators in response to said hard stop force reading.

9. A method of detecting a stuck condition for a medical instrument, the method comprising:
while a medical instrument is retracted in a dithering motion, determining that a force on a component of the medical instrument is greater than a predetermined force threshold;
in response to the determination that the force is greater than the predetermined force threshold, initiating a timer;
determining that the timer has passed a predetermined time threshold; and
in response to the determination that the timer has passed the predetermined time threshold, initiating a responsive action.

10. The method of claim 9, wherein the responsive action involves generating a warning indicating that the medical instrument is in a stuck state.

11. The method of claim 9, wherein the responsive action involves halting retraction of the medical instrument.

12. The method of claim 9, further comprising initiating dithering of one or more components of the medical instrument in response to a determination that a portion of the medical instrument is positioned within a sticking hazard zone.

13. The method of claim 12, further comprising determining the sticking hazard zone based at least in part on a position of a distal end of a sheath in which the medical instrument is a least partially disposed.

14. The method of claim 9, further comprising resetting the timer in response to a determination that the force has fallen below the predetermined force threshold prior to the timer passing the predetermined time threshold.

15. A robotic system comprising:
one or more robotic manipulators;
one or more actuators associated with at least one of the one or more robotic manipulators and configured to cause axial movement of at least one of an endoscope, a sheath of a basket device disposed at least partially within the endoscope, or tines of the basket device;
one or more sensors associated with the one or more robotic manipulators and configured to generate signals indicating a force experienced by the one or more actuators; and

US 12,653,637 B2

47 control circuitry communicatively coupled to the one or
   more robotic manipulators and the one or more sensors
   and configured to:
   cause the basket device to advance and retract in a
      dithering motion;
   while the basket device is moving in the dithering
      motion, receive the signals from the one or more
      sensors indicating the force experienced by the one
      or more actuators;
   determine that the force is greater than a predetermined
      force threshold;
   in response to the determination that the force is greater
      than the predetermined force threshold, initiate a
      timer;
   determine that the timer has passed a predetermined
      time threshold; and
   execute a responsive action in response to the deter-
      mination that the timer has passed the predetermined
      time threshold.
16. The robotic system of claim 15, wherein the respon-
sive action involves generating a warning indicating that the
basket device is in a stuck state.

17. The robotic system of claim 15, wherein the respon-
sive action involves halting retraction of at least one of the
endoscope or the basket device.

18. The robotic system of claim 15, wherein the control
circuitry is further configured to initiate dithering of at least
one of the endoscope, the sheath of the basket device, or
tines of the basket device in response to a determination that
a portion of the basket device is positioned within a sticking
hazard zone.

19. The robotic system of claim 18, wherein the control
circuitry is further configured to determine the sticking
hazard zone based at least in part on a position of a distal end
of a sheath in which the endoscope is a least partially
disposed.

20. The robotic system of claim 15, wherein the control
circuitry is further configured to reset the timer in response
to a determination that the force has fallen below the
predetermined force threshold prior to the timer passing the
predetermined time threshold.

* * * * *